(12) United States Patent
Wen et al.

(10) Patent No.: US 9,394,327 B1
(45) Date of Patent: Jul. 19, 2016

(54) NUCLEOSIDE CRYSTALS, CRYSTAL NUCLEATION AND GROWTH CONTROL WITH ANTIFREEZE PROTEINS

(71) Applicant: The Trustees of California State University, Los Angeles, CA (US)

(72) Inventors: Xin Wen, Alhambra, CA (US); Sen Wang, Alhambra, CA (US)

(73) Assignee: The Trustees of California State University, Los Angeles, CA (US)

(*) Notice: Subject to any disclaimer, the term of this patent is extended or adjusted under 35 U.S.C. 154(b) by 245 days.

(21) Appl. No.: 13/843,142

(22) Filed: Mar. 15, 2013

(51) Int. Cl.
*A61K 31/10* (2006.01)
*C07H 1/06* (2006.01)
*C07H 19/06* (2006.01)
*G01N 33/483* (2006.01)

(52) U.S. Cl.
CPC ............... *C07H 1/06* (2013.01); *C07H 19/06* (2013.01); *G01N 33/483* (2013.01)

(58) Field of Classification Search
CPC .................................................. A61K 31/10
USPC .......................................................... 436/4
See application file for complete search history.

(56) References Cited

U.S. PATENT DOCUMENTS

| | | | |
|---|---|---|---|
| 4,853,439 A | 8/1989 | Barabas | |
| 5,122,543 A * | 6/1992 | Khanna | A61K 9/0095 514/217 |
| 5,358,931 A * | 10/1994 | Rubinsky et al. | 514/17.4 |
| 5,547,857 A * | 8/1996 | Maruyama et al. | 435/87 |
| 5,869,092 A * | 2/1999 | Hays | A61K 9/127 424/450 |
| 5,891,558 A * | 4/1999 | Bell | A61L 27/46 424/425 |
| 5,928,877 A * | 7/1999 | Lusk | C07K 14/461 435/14 |
| 6,303,388 B1 * | 10/2001 | Fahy | A01N 1/02 252/70 |
| 6,547,971 B2 * | 4/2003 | Breen et al. | 210/764 |
| 6,887,984 B2 * | 5/2005 | Berry | C07K 14/195 426/656 |
| 7,700,718 B2 * | 4/2010 | Mie et al. | 530/324 |
| 8,450,089 B2 * | 5/2013 | Ward et al. | 435/113 |
| 2003/0008006 A1 * | 1/2003 | Puthli | A61K 9/0004 424/473 |
| 2003/0111638 A1 * | 6/2003 | Fahy | 252/70 |
| 2003/0159641 A1 * | 8/2003 | Sanjoh et al. | 117/2 |
| 2005/0161631 A1 | 7/2005 | Walker et al. | |
| 2005/0181041 A1 * | 8/2005 | Goldman | A61K 9/145 424/456 |
| 2005/0186636 A1 * | 8/2005 | Yang et al. | 435/7.1 |
| 2006/0009435 A1 * | 1/2006 | Kaspi | A61K 9/0075 514/179 |
| 2007/0134647 A1 * | 6/2007 | Mie et al. | 435/2 |
| 2008/0076670 A1 * | 3/2008 | Sivan | G01N 33/5438 506/9 |
| 2011/0177173 A1 * | 7/2011 | Ward et al. | 424/722 |
| 2013/0139749 A1 * | 6/2013 | Betzel et al. | 117/69 |

FOREIGN PATENT DOCUMENTS

JP          2-23882      * 1/1990

OTHER PUBLICATIONS

Hunt, D. J. et al, Acta Crystallographica 1969 B25, 2144-2152.*
Rodriguez-Hornedo, N. et al, Journal of Pharmaceutical Sciences 1999, 88, 651-660.*
Threlfall, T., Organic Process Research & Development 2000, 4, 384-390.*
Kawahara, H. et al, Current Microbiology 2001, 43, 365-370.*
Kawahara, H., Journal of Bioscience and Bioengineering 2002, 94, 492-496.*
Fujiwara, M. et al, Journal of Process Control 2005, 15, 493-504.*
Doxey, A. C. et al, Nature Biotechnology 2006, 24, 852-855.*
Kawwahara, H. et al, CryoLetters 2007, 28, 39-49.*
Desgranges, C. et al, Physical Review Letters 2007, 98, 235502, 4 pages.*
Simonelli, A. P. et al, Journal of Pharmaceutical Sciences 1970, 59, 633-638.*
Sekikawa, H. et al, Chemical and Pharmaceutical Bulletin 1978, 26, 118-126.*
Busch, N. et al, Journal of Clinical Investigation 1995, 96, 3009-3015.*
DeOliveira, D. B. et al, Journal of the American Chemical Society 1997, 119, 10627-10631.*
Gronwald, W. et al, Biochemistry 1998, 37, 4712-4721.*
Raghavan, S. L. et al, International Journal of Pharmaceutics 2001, 212, 213-221.*
Achenbach, J. C. et al, European Journal of Biochemistry 2002, 269, 1219-1226.*
Zeng, H. et al, Journal of the American Chemical Society 2006, 128, 2844-2850.*
Ishida, H. et al, Journal of Pharmaceutical Sciences 2007, 96, 1131-1138.*
Lindfors, L. et al, Journal of Colloid and Interface Science 2008, 325, 404-413.*
Ziller, K. H. et al, Drug Development and Industrial Pharmacy 1988, 14, 2341-2370.*
Aakeroy, C. B. et al, Chemical Society Reviews, 1993, 397-407.*
Yoshioka, M. et al, Journal of Pharmaceutical Sciences 1995, 84, 983-986.*
Ma, X. et al, International Journal of Pharmaceutics 1996, 142, 115-119.*

(Continued)

*Primary Examiner* — Arlen Soderquist
(74) *Attorney, Agent, or Firm* — Grace Liu

(57) ABSTRACT

The uses of antifreeze proteins (AFPs), including polypeptides, peptides, fragments of AFPs, and mimicries of AFPs, as highly efficient additives for crystal growth control are provided. AFPs are demonstrated to efficiently inhibit the nucleation of commercially and pharmaceutically important compounds (e.g., nucleosides, sugars, salts), increase the supersaturation of their solutions, modify their crystal habits, and result in novel morphologies.

11 Claims, 18 Drawing Sheets

(56) References Cited

OTHER PUBLICATIONS

Taylor, L. S. et al, Pharmaceutical Ressearch 1997, 14, 1691-1698.*
Kachrimanis, K. et al, Journal of Pharmacy and Pharmacology 1999, 51, 1219-1227.*
Knight, C. A., Nature 2000, 406, 249-250.*
Liou, Y.-C. et al, Nature 2000, 406, 322-324.*
Garekani, H. A. et al, International Journal of Pharmaceutics 2000, 208, 87-99.*
Prasad, K. V. R. et al, International Journal of Pharmaceutics 2001, 215, 29-41.*
Tiwary, A. K., Drug Development and Industrial Pharmacy 2001, 27, 669-709.*
Rasenack, N. et al, International Journal of Pharmaceutics 2002, 245, 9-24.*
Weissbuch, I. et al, Crystal Growth & Design 2003, 3, 125-150.*
Rozenberg, M. et al, Physical Chemistry Chemical Physics 2003, 5, 1533-1535.*
Saeedi, M. et al, DARU Journal of Pharmaceutical Sciences 2003, 11, 106-114.*
Rozenberg, M. et al, Spectrochimica Acta Part A 2005, 61, 733-741.*
Mirmehrabi, M. et al, Crystal Growth & Design 2005, 6, 141-149.*
Vega, D. R. et al, International Journal of Pharmaceutics 2007, 328, 112-118.*
Xie, S. et al, Crystal Growth & Design 2010, 10, 3363-3371.*
Choi, H. et al, Journal of Pharmaceutical Sciences 2012, 101, 2941-2951.*
Ko, T.-P. et al, Biophysical Journal 2003, 84, 1228-1237.*
Wang, S. et al., "Expanding the molecular recognition repertoire of antifreeze polypeptides: effects on nucleoside crystal growth," Chem. Comm. 2012, 48, 11555-11557 (with supporting information).
Unknown, Clathrate hydrate, Wikipedia, https://en.wikipedia.org/wiki/Clathrate_hydrate, accessed Dec. 23, 2015.
Unknown, casodex (Bicalutamide) tablet, AstraZeneca Pharnaceuticals LP, http://dailymed.nlm.nih.gov/dailymed/archives/fdaDrugInfo.cfm?archiveid=5071, Aug. 2007.
Berg, et al. Biochemistry, 5th Ed. New York: WH Freeman, 2002. sections 5.1.1 and 5.1.2 downloaded from http://www.ncbi.nlm.nih.gov/books/NBK22490.
Unknown, Nucleoside, Wikipedia, https://en.wikipedia.org/wiki/Nucleoside, accessed Dec. 23, 2015.
Chen, et al, Proc. Natl. Acad. Sci. USA, 99(13): 9031-9036, 2002.
Unknown, Inosine. Wikipedia. https://en.wikipedia.org/wiki/Inosine, accessed Dec. 23, 2015.
Raymond, JA and Devries, AL, Proc Natl Acad Sci USA, 74(6): 2589-2593, 1977.
Jia, Z and Davies, PL. Trends in Biochemical Sciences, 27(2), 101-106, 2002.

\* cited by examiner

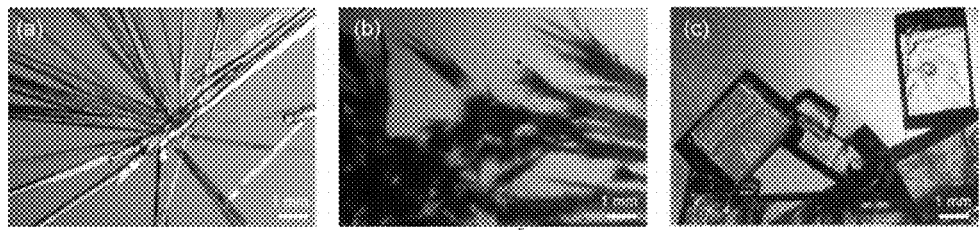

Optical micrographs of the finally achieved m⁵U solids. (a) Needle-like orthorhombic m⁵U crystals, (b) reed-like amorphous m⁵U precipitates obtained in the presence of DAFP-1, (c) normal orthorhombic m⁵U crystals obtained in the presence of DAFP-1 and m⁵U seed crystals.

FIGS. 1(a)-(c)

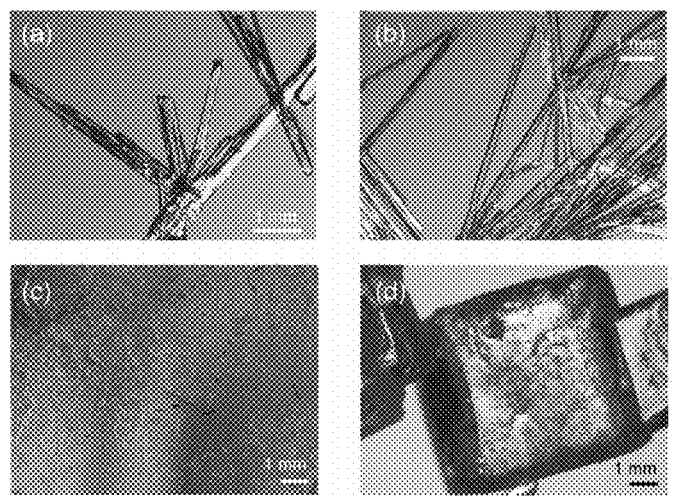

Optical micrographs of the finally achieved crystals or amorphous solids of m⁵U: (a) needle-shaped m⁵U crystals obtained in the presence of BSA, (b) needle-shaped m⁵U crystals obtained in the presence of the denatured DAFP-1 with completely reduced disulfide bonds, (c) gel-like amorphous m⁵U solids obtained in the presence of type III AFP, (d) normal orthorhombic m⁵U crystals obtained in the presence of type III AFP and seed m⁵U crystals in a saturated m⁵U solution.

FIGS. 2(a)-(d)

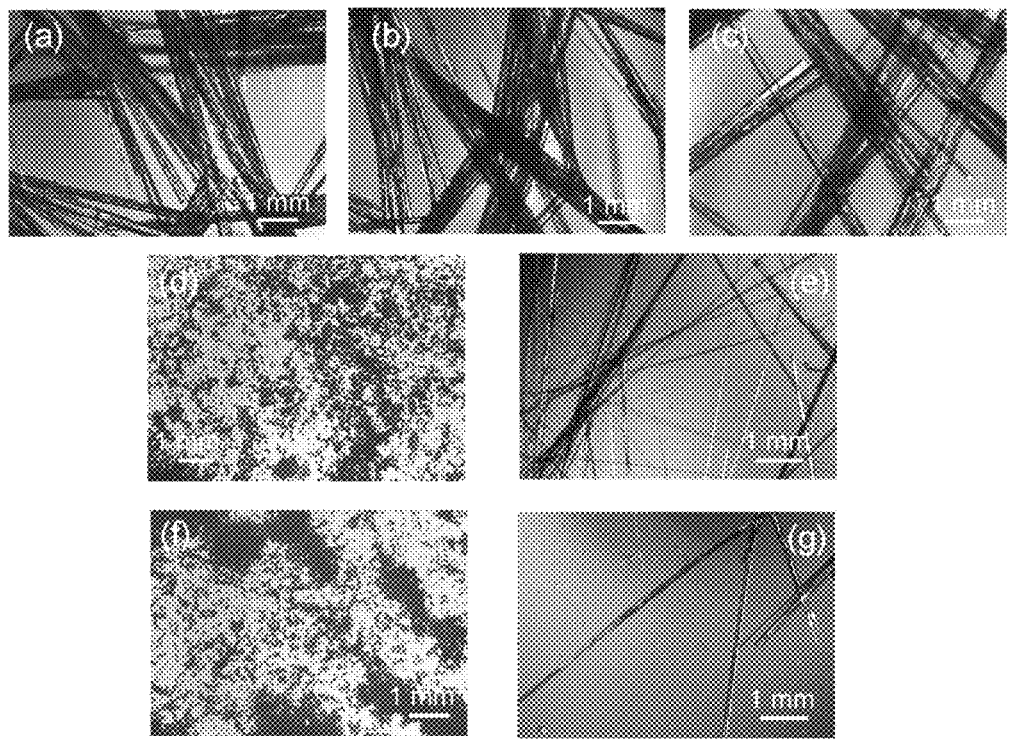

Optical micrographs of the final achieved crystals or amorphous solids of C: (a) needle-like C crystals, (b) needle-like C crystals obtained in the presence of BSA, (c) needle-like C crystals obtained in the presence of the denatured DAFP-1 with completely reduced disulfide bonds, (d) powder-like amorphous C solids obtained in the presence of DAFP-1, (e) hair-like C crystals obtained in the presence of DAFP-1 and seed C crystals in a saturated C solution, (f) powder-like amorphous C solids obtained in the presence of type III AFP, (g) hair-like C crystals obtained in the presence of type III AFP and seed C crystals in a saturated C solution.

FIGS. 3(a)-(g)

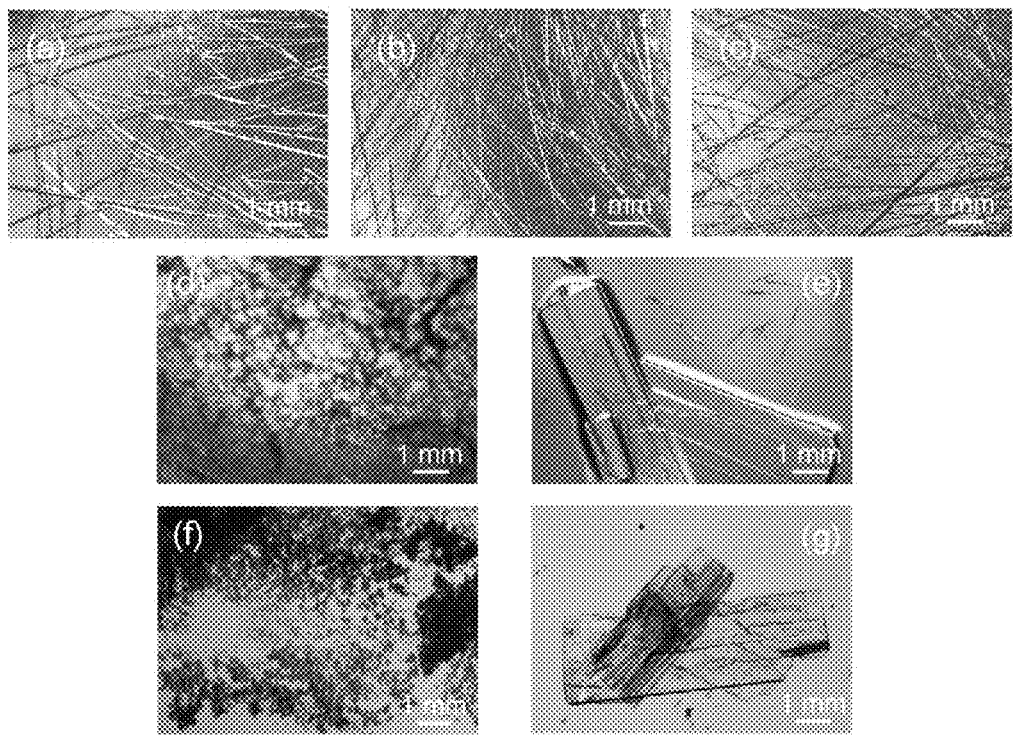

Optical micrographs of the final achieved crystals or amorphous solids of I: (a) hair-like I crystals, (b) hair-like I crystals obtained in the presence of BSA, (c) hair-like I crystals obtained in the presence of the denatured DAFP-1 with completely reduced disulfide bonds, (d) powder-like amorphous I solids obtained in the presence of DAFP-1, (e) plate-like I crystals obtained in the presence of DAFP-1 and seed I crystals in a saturated I solution, (f) powder-like amorphous I solids obtained in the presence of type III AFP, (g) plate-like I crystals obtained in the presence of type III AFP and seed I crystals in a saturated I solution.

FIGS. 4(a)-(g)

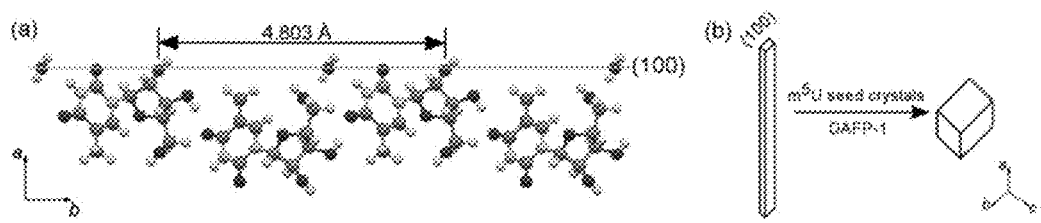

(a) The structure of the (100) face of $m^5U$ crystals (carbon, grey; oxygen, red; hydrogen, white; nitrogen, blue). The $c$-axis points into the plane of the paper. (b) Schematic representation: the growth rate along the $a$-axis is much faster than that along the $b$- or $c$-axis in a typical $m^5U$ crystal habit, while the growth along the $a$-axis is significantly inhibited in the presence of DAFP-1 becoming less than that along the $b$- or $c$-axis.

FIG. 5

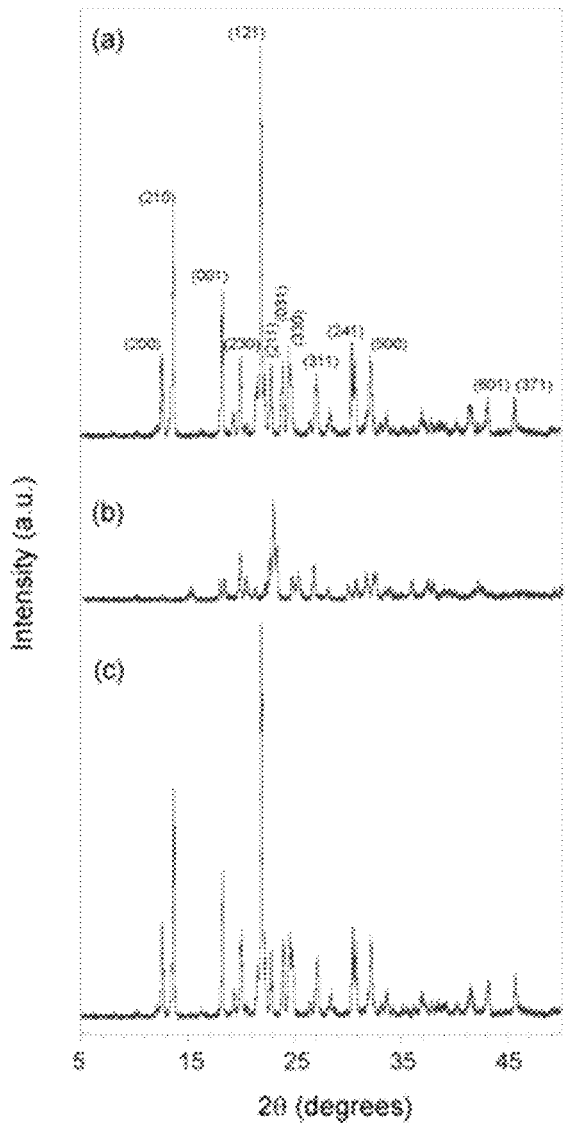
Overlay of representative powder XRD profiles of the samples from (a) needle-like crystalline m$^5$U, (b) reed-like amorphous m$^5$U precipitates obtained in the presence DAFP-1, and (c) normal orthorhombic crystalline m$^5$U modified by DAFP-1. Major crystalline peaks in (a) are labeled with miller indexes (*hkl*).
FIGS. 6(a)-(c)

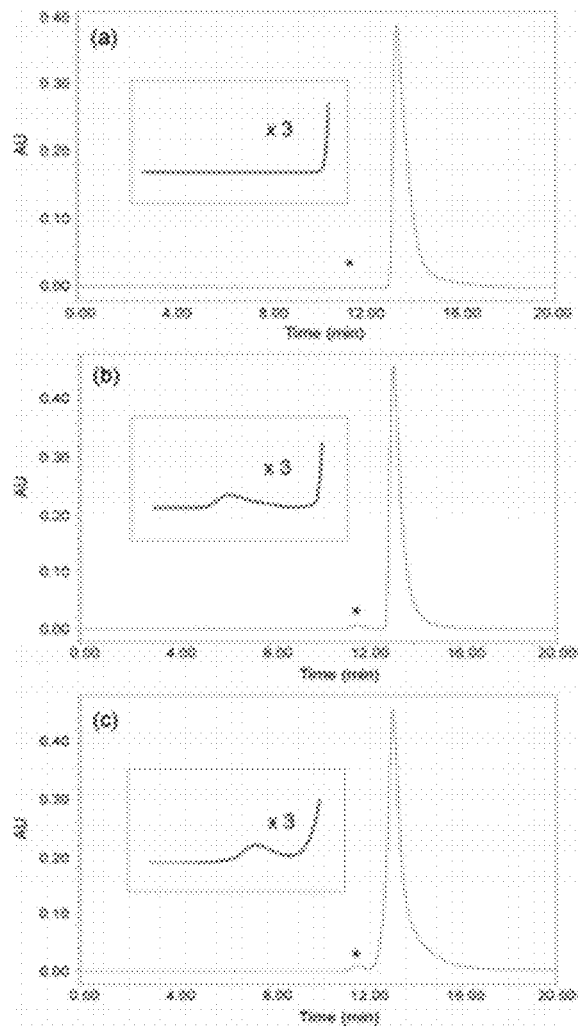

Gel filtration HPLC analysis of the crystals of $m^5U$ monitored at 280 nm. Typical chromatograms of (a) crystalline $m^5U$ obtained in the presence of denatured DAFP-1, (b) reed-like amorphous $m^5U$ precipitates obtained in the presence of DAFP-1, (c) normal orthorhombic crystalline $m^5U$ modified using DAFP-1 in the presence of $m^5U$ seed crystals. The retention times for $m^5U$ and DAFP-1 are 13.1 min and 11.5 min, respectively. Insets: enlarged portions (denoted by asterisks).

FIGS. 7(a)-(c)

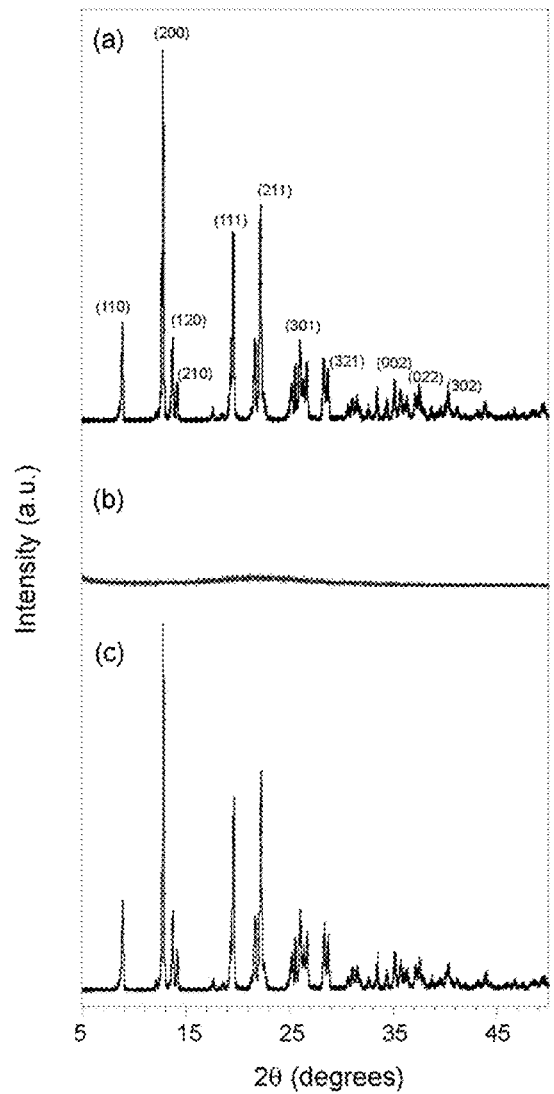
Overlay of representative PXRD profiles of the samples from (a) needle-like C crystals, (b) amorphous C (obtained in the presence DAFP-1), and (c) hair-like C crystals (modified by DAFP-1). Major crystalline peaks in (a) are labeled with miller indexes (*hkl*).
FIGS. 8(a)-(c)

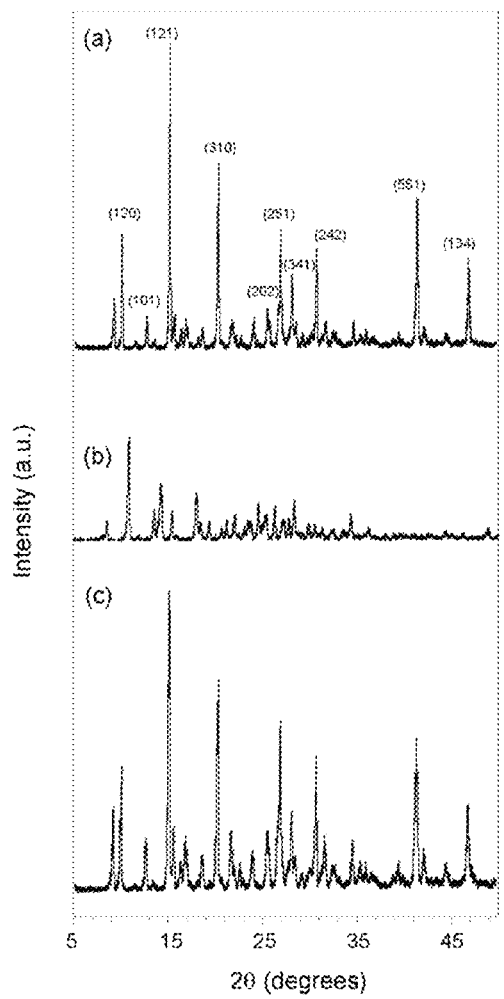
Overlay of representative PXRD profiles of the samples from (a) hair-like I crystals, (b) amorphous I (obtained in the presence DAFP-1), and (c) plate-like I crystals (modified by DAFP-1). Major crystalline peaks in (a) are labeled with miller indexes (*hkl*).
FIGS. 9(a)-(c)

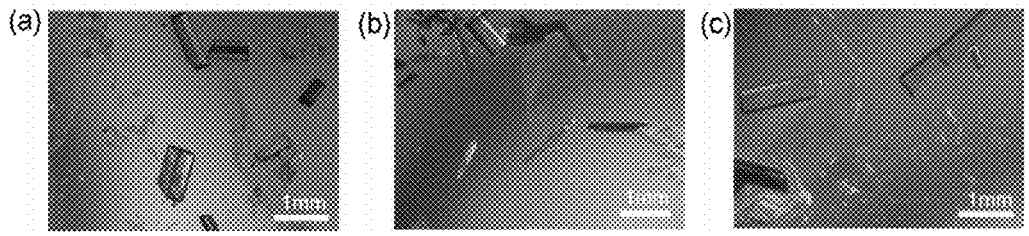

Optical micrographs of the final achieved thymine crystals (a) in the absence of AFPs, (b) in the presence of DAFP-1, (c) in the presence of type III AFP.

FIGS. 10(a)-(c)

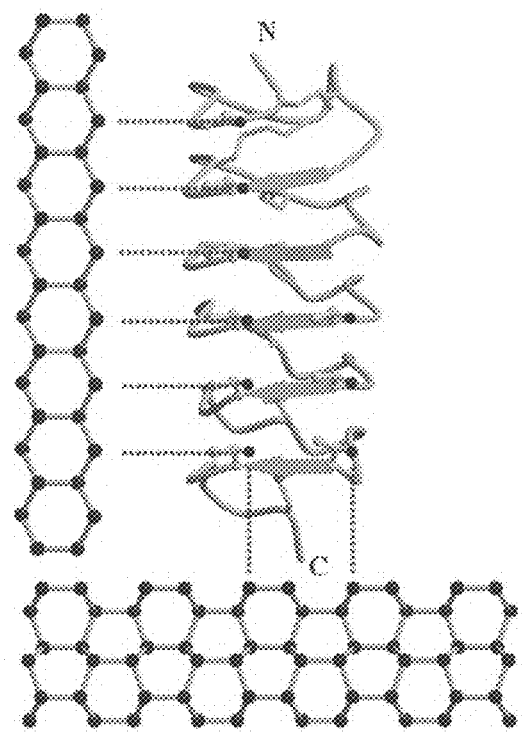

Model of a *Dendroides canadensis* antifreeze protein (AFP) isoform aligned to the prism face of ice. The ribbon illustration of AFP isoform 1 from the beetle *D. canadensis* shows the ice-binding β sheet (green arrows) made up of aligned Thr–Cys–Thr motifs.

FIG. 11

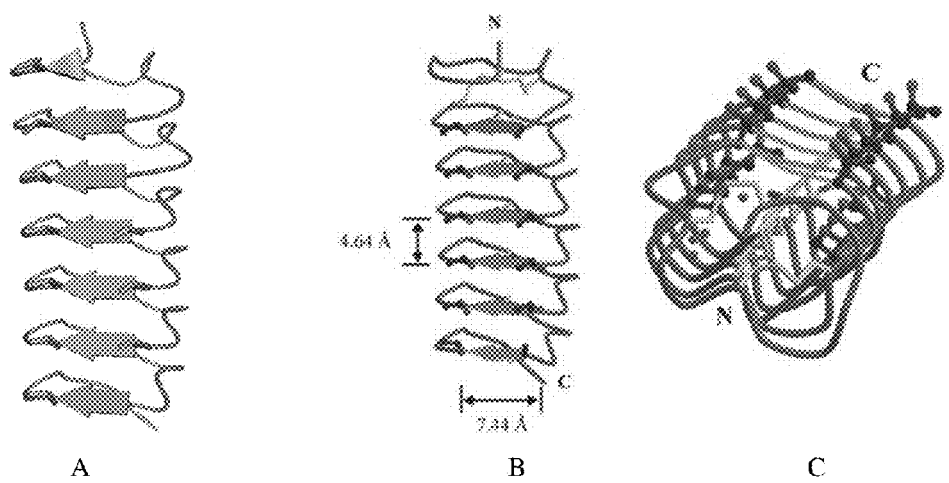

A B C

Views of the tertiary structure of DAFP-1 from *Dendroides canadensis*. DAFP-1 consists of seven repeat units. The putative ice-binding threonine residues are indicated as sticks. The average distance of the side-chain oxygen atoms in the threonine residues in the adjacent loops is 4.74 Å matching well to 4.80 Å, the unit-cell dimension along the $c$ axis in $m^5U$ form I crystal.

FIGS. 12(a)-(c)

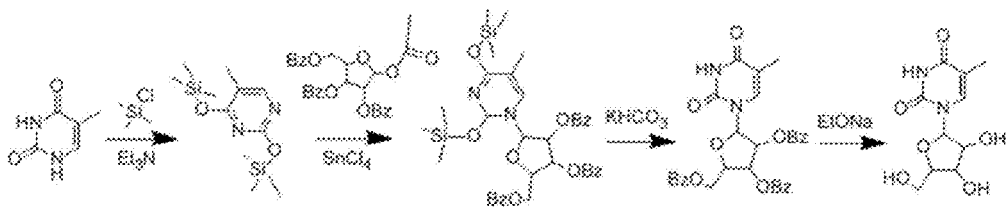

Synthesis Strategy for 5-Methyluridine. The final product was characterized using LC/ESI-MS and NMR since o,o'-bis(trimethylsilyl)thymine and protected m$^5$U intermediates do not dissolve well in common solvents. Mass spectra were obtained using a Waters 2795 HPLC system with ZQ single quadrupole MS and an electrospray ionization source. Samples were introduced using loop injection. The calculated mass of m$^5$U ($C_{10}H_{14}N_2O_6$) is 258.2 and the [M + H]$^+$ ion of m$^5$U is found at $m/z$ 259.2. $^1$H and $^{13}$C NMR spectra were obtained in $D_2O$ at 25 °C using a Bruker 400 MHz spectrometer.

$^1$H NMR (400 MHz, $D_2O$) (Appendix 15): δ ppm = 7.61 (s, C=CH), 5.83 (d, $^3$J(H,H) = 4.61, OCH), 4.25 (t, $^3$J(H,H) = 4.12, HOCH*CHOHCHO(N)), 4.15 (t, $^3$J(H,H) = 4.12, HOCHCH*OHCHO(N)), 4.04 (m, HOCH$_2$CH*CHOH), 3.78 (dd, $^2$J(H,H) = 7.5, $^3$J(H,H) = 2.5, HOCH$_2$).
$^{13}$C NMR (100.64 MHz, $D_2O$) (Appendix 16): δ ppm = 165.79 (C*OCCH$_3$), 151.58 (NCON), 137.36 (NC=), 111.45 (CH$_3$C*=), 88.91 (OCN), 84.10 (C*CH$_2$OH), 73.43 (NCC*OH), 69.34 (HOCC*OH), 60.66 (CH$_2$OH), 11.49 (CH$_3$).

FIG. 13

$^1$H NMR spectrum of m$^5$U in D$_2$O (400 MHz)

$^{13}$C NMR spectrum of m$^5$U in D$_2$O (100.64 MHz)

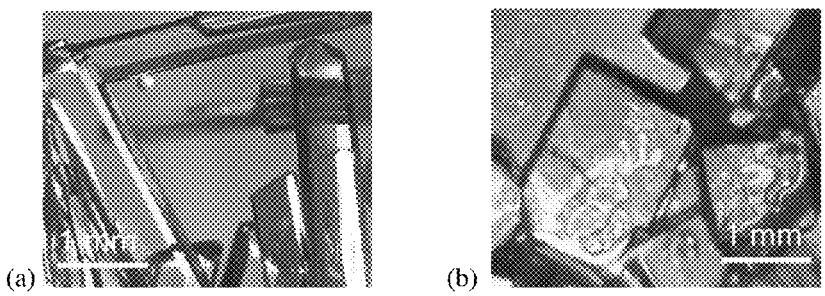
Optical micrographs of the finally achieved m$^5$U crystals: (a) needle-shaped m$^5$U hemihydrates (form I); (b) block-shaped m$^5$U dihydrates (form II) obtained in the presence of DAFP-1.
FIGS. 16(a)-(b)
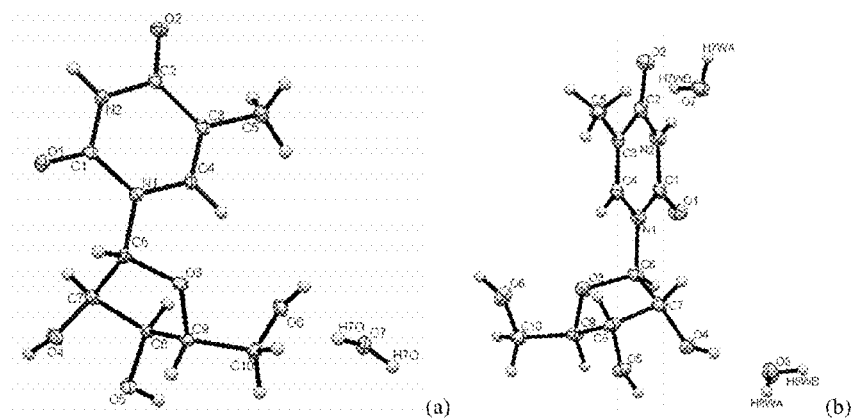
Representative molecules in (a) m$^5$U form I (hemihydrate) and (b) m$^5$U form II (dihydrate)
FIGS. 17(a)-(b)

Overlay of unique molecules in the crystal structure of m5U form I (all are in a red color) and form II (all are in a blue color except that hydrogen atoms are in a gray color).

Packing diagrams of m$^5$U form I (a and b) and form II (c and d). Dotted lines represent intermolecular hydrogen bonding in the crystals.

FIGS. 19(a)-(d)

DSC thermograms (exo up) of form I (a) and form II (b) of m⁵U.

Comparison of relative enthalpies for the phase transitions of form I and form II m⁵U.

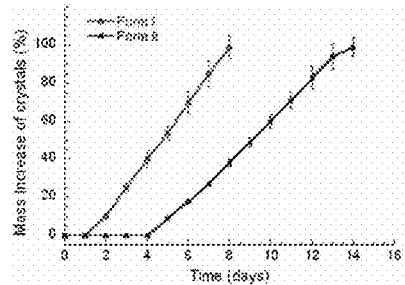
Comparison of crystallization kinetics of form I and form II of $m^5U$. Mass increase of crystals during the crystallization processes was used to estimate relative crystallinity.
FIG. 22
(a)
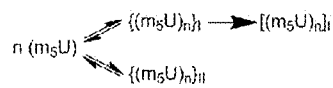
(b)
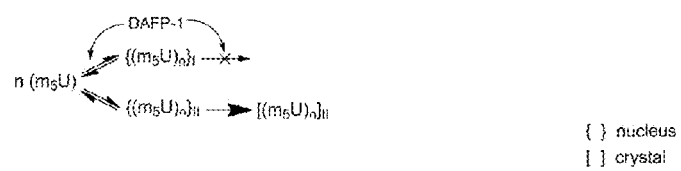
{ } nucleus
[ ] crystal
Suggested mechanism for crystallization of $m^5U$ (a) and selective crystallization of $m^5U$ form II using DAFP-1 (b).
FIGS. 23(a)-(b)

Trehalose
(a) (b)

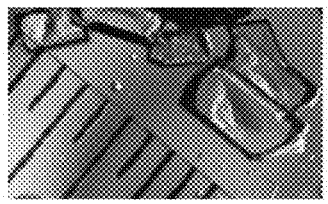 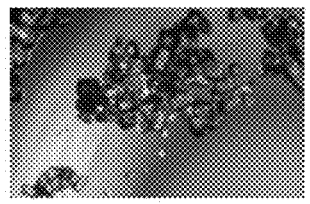

Optical micrographs of trehalose dihydrate crystals: (a) block-like trehalose dihydrate crystals; (b) trehalose dihydrate crystals with dramatically decreased sizes obtained in the presence of DAFP-1 (from 1 - 1.5 mm to 0.1 - 0.3 mm). The scale bars are the same for both graphs as shown in graph (a).

FIGS. 24(a)-(b)

$CuSO_4 \cdot 5 H_2O$
(a) (b)

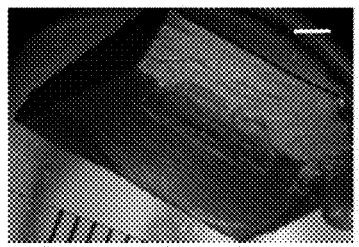 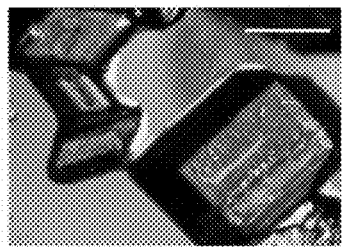

Optical micrographs of copper sulfate pentahydrate ($CuSO_4 \cdot 5 H_2O$) crystals: (a) bright blue stone-like $CuSO_4 \cdot 5 H_2O$ crystals; (b) bright blue stone-like $CuSO_4 \cdot 5 H_2O$ crystals with dramatically decreased sizes obtained in the presence of DAFP-1. The scale bars shown in white on top of the graphs are 1 mm.

FIGS. 25(a)-(b)

NUCLEOSIDE CRYSTALS, CRYSTAL NUCLEATION AND GROWTH CONTROL WITH ANTIFREEZE PROTEINS

FUNDING STATEMENT

This work was supported in full by NIH Grant GM086249, and in part by Research Corporation for Science Advancement Cottrell College Science Award CC10492.

BACKGROUND

Crystal growth control is essential in various fields of science and technology (e.g., chemistry, materials science, pharmaceutical development). For instance, changes in the size and shape of crystals of pharmaceutical compounds can impact their bioavailability, chemical stability, and production efficiency. Traditional methods to control crystallization usually include the alterations of temperature, solvent, supersaturation, and seeding conditions. A number of recent methods, such as using tailor-made additives, ledge-directed epitaxy, polymer microgel, polymer heteronuclei, capillaries, porous materials, and laser-induced nucleation have been developed and employed in the crystallization process of certain compounds to select favored and/or discover new crystalline forms of the compounds.

The concept of molecular recognition has been successfully used to elucidate the effects of additives (foreign ions or molecules) on crystal growth. Peptides and proteins are often used in vivo and in vitro to control the growth of minerals and produce new forms of solids with different physicochemical properties. For example, peptide additives in either α-helix or β-sheet arrangement designed to interact with calcite crystal faces have been demonstrated to control calcite crystal habit. Size and shape control of organic crystals, however, is more difficult due to their anisotropic properties (different atomic arrangements in three dimensions).

Although tremendous effort has been devoted to understanding the crystallization process and selective crystallization, the crystallization control process remains largely trial-and-error, experiencing substantial difficulties in exclusive production of the desired forms as well as the production of both thermodynamically and kinetically less favored forms. Moreover, much less progress has been made in additive-controlled organic crystallization than in additive-controlled inorganic crystallization, and the selective production of organic single crystals with defined crystal phase and morphology still remains an enigma. For example, nucleosides and their analogues, an important class of pharmaceutical compounds, have been used as viral mutagens, drugs for induction therapy, effective treatment of lymphoproliferative disorders, and spinal cord injury, however little is known about their size and shape control using additives.

Antifreeze polypeptides (AFPs) are a structurally diverse group of proteins found in many cold-adapted organisms to protect them from freeze damage through a noncolligative manner, providing an intriguing example of ice crystal growth control. AFPs can bind to specific faces of ice crystals and modify the habit of the ice crystals. Their affinity to ice depends on hydrogen bonding and hydrophobic interactions, unlike most protein-mineral interactions where ionic interactions often play a dominant role. Ice and clathrate hydrates (ice-like crystalline solids) are known to be inhibited and modified by AFPs. Although ice is known with many polymorphs, studies on ice morphs induced by AFPs are lacking. Until now, AFP studies focused on the isolation, antifreeze activity, structure determination, and ice or ice-like solid binding of AFPs. Detailed mechanisms of AFPs still remain unknown.

SUMMARY OF THE INVENTION

AFPs previously have been used for their antifreeze properties, largely to control ice and ice-like crystalline growth. We have found that AFPs can efficiently inhibit nucleation and modify single crystal growth of compounds having non-ice-like crystalline structures such as nucleosides, sugars, and salts (e.g., halides, carboxylates, phosphates, hydrogen/dihydrogen phosphates, sulfates, etc.), despite their being structurally different from ice and ice-like crystalline structures. This invention also presents novel examples of effective control of crystal growth of organic compounds by AFP additives. Moreover, AFPs can induce new crystalline forms with altered crystal shapes, e.g., via selective growth of hydrates and polymorphs of hydroxyl compounds.

BRIEF DESCRIPTION OF THE DRAWINGS

FIGS. 1(a)-(c) show optical micrographs of the finally achieved $m^5U$ solids. (a) Needle-like orthorhombic $m^5U$ crystals, (b) reed-like amorphous $m^5U$ precipitates obtained in the presence of DAFP-1, (c) normal orthorhombic $m^5U$ crystals obtained in the presence of DAFP-1 and $m^5U$ seed crystals.

FIGS. 2(a)-(d) show optical micrographs of the finally achieved crystals or amorphous solids of $m^5U$: (a) needle-shaped $m^5U$ crystals obtained in the presence of BSA, (b) needle-shaped $m^5U$ crystals obtained in the presence of the denatured DAFP-1 with completely reduced disulfide bonds, (c) gel-like amorphous $m^5U$ solids obtained in the presence of type III AFP, (d) normal orthorhombic $m^5U$ crystals obtained in the presence of type III AFP and seed $m^5U$ crystals in a saturated $m^5U$ solution.

FIGS. 3(a)-(g) show optical micrographs of the final achieved crystals or amorphous solids of C: (a) needle-like C crystals, (b) needle-like C crystals obtained in the presence of BSA, (c) needle-like C crystals obtained in the presence of the denatured DAFP-1 with completely reduced disulfide bonds, (d) powder-like amorphous C solids obtained in the presence of DAFP-1, (e) hair-like C crystals obtained in the presence of DAFP-1 and seed C crystals in a saturated C solution, (f) powder-like amorphous C solids obtained in the presence of type III AFP, (g) hair-like C crystals obtained in the presence of type III AFP and seed C crystals in a saturated C solution.

FIGS. 4(a)-(g) show optical micrographs of the final achieved crystals or amorphous solids of I: (a) hair-like I crystals, (b) hair-like I crystals obtained in the presence of BSA, (c) hair-like I crystals obtained in the presence of the denatured DAFP-1 with completely reduced disulfide bonds, (d) powder-like amorphous I solids obtained in the presence of DAFP-1, (e) plate-like I crystals obtained in the presence of DAFP-1 and seed I crystals in a saturated I solution, (f) powder-like amorphous I solids obtained in the presence of type III AFP, (g) plate-like I crystals obtained in the presence of type III AFP and seed I crystals in a saturated I solution.

FIG. 5 shows (a) The structure of the (100) face of $m^5U$ crystals (carbon, grey; oxygen, red; hydrogen, white; nitrogen, blue). The c-axis points into the plane of the paper. (b) Schematic representation: the growth rate along the a-axis is much faster than that along the b- or c-axis in a typical $m^5U$ crystal habit, while the growth along the a-axis is significantly inhibited in the presence of DAFP-1 becoming less than that along the b- or c-axis.

FIGS. 6(a)-(c) show representative powder XRD profiles of the samples from needle-like crystalline $m^5U$ (a), reed-like amorphous $m^5U$ precipitates obtained in the presence DAFP-1 (b), and normal orthorhombic crystalline $m^5U$ modified by DAFP-1(c), respectively. Major crystalline peaks in (a) are labeled with miller indexes (hkl).

FIGS. 7(a)-(c) show gel filtration HPLC analyses of the crystals of $m^5U$ monitored at 280 nm. FIG. 7(a) shows typical chromatograms of crystalline $m^5U$ obtained in the presence of denatured DAFP-1, FIG. 7(b) shows typical chromatograms of reed-like amorphous $m^5U$ precipitates obtained in the presence of DAFP-1, FIG. 7(c) shows typical chromatograms of normal orthorhombic crystalline $m^5U$ modified using DAFP-1 in the presence of $m^5U$ seed crystals. The retention times for $m^5U$ and DAFP-1 are 13.1 min and 11.5 min, respectively. Insets: enlarged portions (denoted by asterisks).

FIGS. 8(a)-(c) show representative PXRD profiles of the samples from needle-like C crystals (a), amorphous C (obtained in the presence DAFP-1) (b), and hair-like C crystals (modified by DAFP-1) (c), respectively. Major crystalline peaks in (a) are labeled with miller indexes (hkl).

FIGS. 9(a)-(c) show representative PXRD profiles of the samples from hair-like I crystals (a), amorphous I (obtained in the presence DAFP-1) (b), and plate-like I crystals (modified by DAFP-1) (c), respectively. Major crystalline peaks in (a) are labeled with miller indexes (hkl).

FIGS. 10(a)-(c) show optical micrographs of the final achieved thymine crystals in the absence of AFPs (a), in the presence of DAFP-1 (b), and in the presence of type III AFP (c), respectively.

FIG. 11 shows model of a *Dendroides canadensis* antifreeze protein (AFP) isoform aligned to the prism face of ice. The ribbon illustration of AFP isoform 1 from the beetle *D. canadensis* shows the ice-binding β sheet (green arrows) made up of aligned Thr-Cys-Thr motifs.

FIG. 12(a) shows view of the tertiary structure of DAFP-1 from *Dendroides canadensis*. DAFP-1 consists of seven repeat units. The putative ice-binding threonine residues are indicated as sticks. The average distance of the side-chain oxygen atoms in the threonine residues in the adjacent loops is 4.74 Å matching well to 4.80 Å, the unit-cell dimension along the c axis in $m^5U$ form I crystal.

FIG. 13 shows a synthesis strategy for 5-methyluridine

FIGS. 16(a)-(b) show optical micrographs of the finally achieved $m^5U$ crystals: (a) needle-shaped $m^5U$ hemihydrates (form I); (b) block-shaped $m^5U$ dihydrates (form II) obtained in the presence of DAFP-1.

FIGS. 17(a)-(b) show representative molecules in $m^5U$ form I (hemihydrate) (a) and $m^5U$ form II (dihydrate) (b).

FIG. 22 shows comparison of crystallization kinetics of form I and form II of $m^5U$. Mass increase of crystals during the crystallization processes was used to estimate relative crystallinity.

FIGS. 23(a)-(b) show suggested mechanism for crystallization of $m^5U$ (a) and selective crystallization of $m^5U$ form II using DAFP-1 (b).

FIGS. 24(a)-(b) show optical micrographs of trehalose dihydrate crystals: (a) block-like trehalose dihydrate crystals; (b) trehalose dihydrate crystals with dramatically decreased sizes obtained in the presence of DAFP-1 (from 1-1.5 mm to 0.1-0.3 mm) The scale bars are the same for both graphs as shown in graph (a).

FIGS. 25(a)-(b) show optical micrographs of copper sulfate pentahydrate ($CuSO_4 \cdot 5 H_2O$) crystals: bright blue stone-like $CuSO_4 \cdot 5 H_2O$ crystals obtained in the absence of additives (a); bright blue stone-like $CuSO_4 \cdot 5 H_2O$ crystals with dramatically decreased sizes, which were obtained in the presence of DAFP-1 (b). The scale bars shown in white on top of the graphs are 1 mm

DETAILED DESCRIPTION

Figure 14:
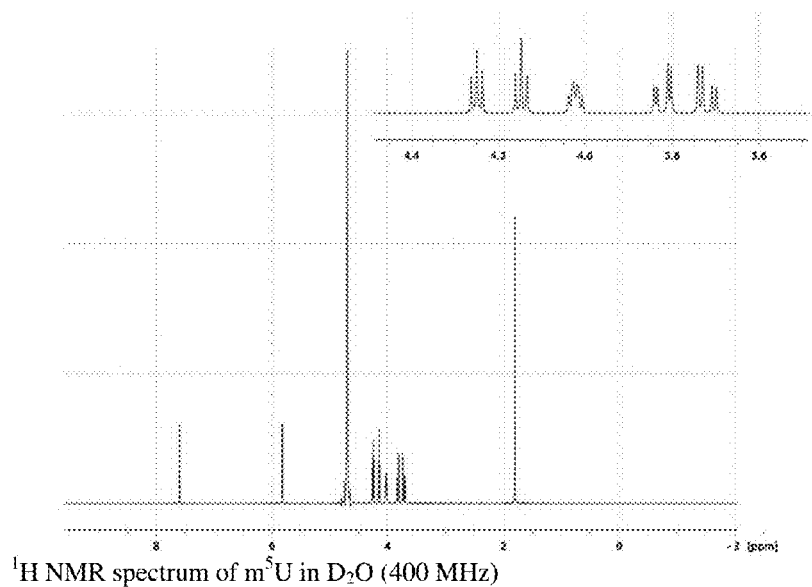
FIG. 14 shows $^1H$ NMR spectrum of the product ($m^5U$) in $D_2O$ (400 MHz)

Throughout this specification, the terms "a" and "an" and variations thereof represent the phrase "at least one." In all cases, the terms "comprising", "comprises" and any variations thereof should not be interpreted as being limitative to the elements listed thereafter. Unless otherwise specified in the description, all words used herein carry their common meaning as understood by a person having ordinary skill in the art. In cases where examples are listed, it is to be understood that combinations of any of the alternative examples are also envisioned. The scope of the invention is not to be limited to the particular embodiments disclosed herein, which serve merely as examples representative of the limitations recited in the issued claims resulting from this application, and the equivalents of those limitations.

Throughout this specification, the following abbreviations and definitions apply: AFP=antifreeze protein; DAFP=*Dendroides canadensis* antifreeze protein; TmAFP=*Tenebrio molito* antifreeze protein; $m^5U$=5-methyluridine; C=cytidine; I=inosine; MALDI-TOF=matrix-assisted laser desorption/ionization time-of-flight; HPLC=high-performance liquid chromatography; SDS-PAGE=sodium dodecyl sulfate polyacrylamide gel electrophoresis; CD=circular dichroism; DSC=differential scanning calorimetry; PXRD=powder X-ray diffraction. The term "AFP" is defined herein by the cumulative group consisting of natural or engineered antifreeze proteins, antifreeze polypeptides and antifreeze peptides, active fragments of antifreeze proteins, antifreeze polypeptides and antifreeze peptides, mimetics of antifreeze proteins, antifreeze polypeptides and antifreeze peptides, their active mimetic fragments, and combinations thereof. The foregoing term "antifreeze" is defined as thermal hysteresis. The term "ice-like crystalline structures" is defined as ice and gas hydrates. The term "critical ratio" is the molar ratio of additive:compound required to completely inhibit the growth of crystals.

Control of crystallization by crystal nucleation and/or growth is essential in various fields of science and technology (e.g., chemistry, materials science, pharmaceutical development). The concept of molecular recognition has been successfully used to elucidate the effects of additives (foreign ions or molecules) on crystal growth. Peptides and proteins are often used in vivo and in vitro to control the growth of minerals and produce new forms of solids with different physicochemical properties. Size and shape control of organic crystals, however, is more difficult due to their anisotropic properties (different atomic arrangements in three dimensions).

Antifreeze polypeptides (AFPs) are a structurally diverse group of proteins found in many cold-adapted organisms (e.g., insect, plant, fungi, protist, bacteria) to protect them from freeze damage through a noncolligative manner, providing an intriguing example of ice crystal growth control. AFPs bind to specific faces of ice crystals and modify the habit of the ice crystals (FIG. 11). Their affinity to ice depends on hydrogen bonding and hydrophobic interactions, unlike most protein-mineral interactions where ionic interactions often play a dominant role. Ice and clathrate hydrates (ice-like crystalline solids) are known to be inhibited and modified by AFPs. Nevertheless, we have now discovered that the recognition ability of AFPs is beyond ice and ice-like crystalline solids.

AFPs have been found to produce inhibitory and habit-modifying effects on the stable nuclei formations and on non-ice-like compounds such as nucleoside crystals. Such effects of AFPs are analogous to their effects on ice despite the large structural differences. For example, ice $I_h$ has a hexagonal structure, while nucleosides $m^5U$, C, and I crystals have orthorhombic structures with different cell dimensions. Effects achieved with these non-ice-like crystals illustrate flexibility in AFP molecular recognition beyond ice and ice-like crystals. Moreover, the effects of AFPs on the nucleoside crystal growth are highly efficient (e.g., less than 1/1000 molar ratio of additive to compound), comparing with other additives on crystal growth control.

Use of AFPs in crystallization processes allows for control and selective crystal growth of polycrystalline ice and other important compounds, such as nucleosides, carbohydrates, salts, and their hydrate forms. Examples of nucleosides include, but are not limited to 5-methyluridine, cytidine, inosine and their analogs; deoxynucleosides and their analogs, including but not limited to adenosine, guanosine, 5-methyluridine, uridine, cytosine, deoxyadenosine, deoxyguanosine, thymidine, deoxyuridine, deoxycytidine, 5-ethyluridine, 5-iodouridine, and compounds having the following general structures:

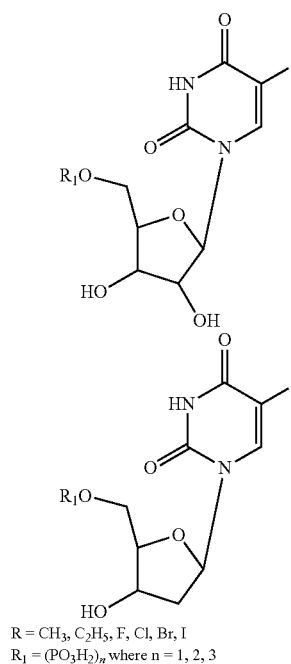

R = CH$_3$, C$_2$H$_5$, F, Cl, Br, I
R$_1$ = (PO$_3$H$_2$)$_n$ where n = 1, 2, 3

Additional suitable compounds and their analogs comprise the following three general components: phosphate, sugar and amine base. Examples of the three components follow.

1. Examples of the phosphate component include, but are not limited to:

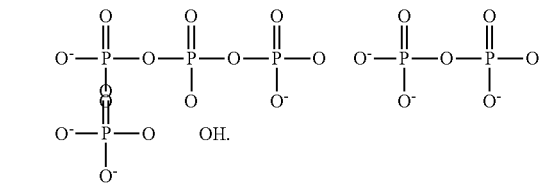

2. Examples of the sugar component include, but are not limited to: any mono-, di-, tri-saccharide/deoxysaccharide and their analogs.

3. Examples of the amine base component include, but are not limited to:

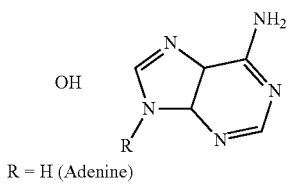

R = H (Adenine)

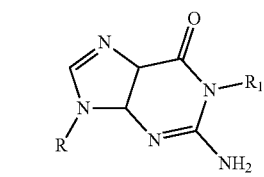

R$_1$ = R = H (Guanine)

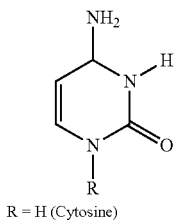

R = H (Cytosine)

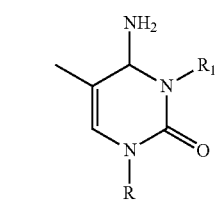

R$_1$ = R = H (Thymine)

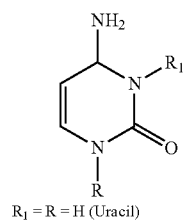

$R_1 = R = H$ (Uracil)

Base or OH or H.

In addition, R and R1 can be any of the substituent groups including CH3, C2H5, F, Cl, Br, I, SMe, COO—, or any group from naturally modified bases.

Examples of carbohydrates include, but are not limited to monosaccharides, disaccharides, trisaccharides, and water (or alcohol) soluble multisaccharides. For example, sugars (trehalose, glucose, fructose, sucrose, lactose, maltose, galactose, 2-deoxy-galactose, a-methyl-D-mammoside, mannose, D-(+)-melibose, and D-(+)-raffinose).

Examples of salts include, but are not limited to Cl⁻, Br⁻, I⁻, F, OH⁻, COO⁻, phosphates, sulfates, and salt hydrates, including, but not limited to NaCl, KCl, $CaCO_3$, $Na_2CO_3$, $Na_3PO_4$, $Na_2HPO_4$, $NaH_2PO_4$, and $CuSO_4$.

Moreover, AFPs may be used as scaffolds to design novel, effective crystal growth inhibitors and modifiers. Most AFPs have at least one-dimensional repeats of the OH binding amino acids, while certain AFPs such as DAFP, TmAFP and others have two-dimensional repeats (adjacent loop and within the same repeat, 4.64 Å and 7.44 Å, respectively, In the case of TmAFP; FIGS. 12(*a*)-(*c*)). Thus, this scaffold pattern can be maintained, with selective exchange of amino acids (e.g., threonines in DAFP or TmAFP can be changed to other amino acids). The resulting engineered proteins may have a wider variety of uses and be designed for use with more diverse crystals forms.

It should be noted that while some of crystal nucleation and growth control appears to be affected at least in part by the "distance matching" dimensions between the non-ice-like compound and the AFP additive as discussed herein, we have obtained similar results for compounds having lattice spaces that do not correspond to AFPs, e.g., cytarabine, trehalose, glucose, xylitol, chloride, bromide, iodide, fluoride, phosphate, sulfate, and carboxylate salts. In the case of the salts, the anions are hydroxide or react similarly to hydroxides (e.g., fluorides, chlorides, bromides, iodides, phosphates, sulfates, and carbolxylates).

Crystal growth at the molecular level can be modeled as a process starting from prenucleation aggregate formation, and then followed by crystal nuclei evolution and macroscopic crystal development. The arrangements and shapes of at least some of these prenucleation aggregates and evolved nuclei are thought to resemble the final crystal structure, the control of which is a decisive step in producing the final crystalline form. Additives usually effect crystal growth by affecting nucleation (e.g., prevent, delay, promote) and/or modifying crystal habit (e.g., adsorbing onto specific crystal growing face(s) and changing the growth rate). Thus, AFPs may be used to produce new forms of compounds that have not been possible to obtain using prior methods.

In addition to the use of AFPs in the manner described herein, it is contemplated also that other parameters known in the art to affect crystal habit, such as temperature, pressure, and solvents may be used in combination with the AFPs in order to optimize desired results.

EXAMPLE 1

In this study, we demonstrate that AFPs can efficiently inhibit the nucleation and modify the single crystal growth of 5-methyluridine ($m^5U$), cytidine (C), and inosine (I). $m^5U$, C, and I are widely used nucleosides in the pharmaceutical industry, but little is known about their size and shape control using additives.

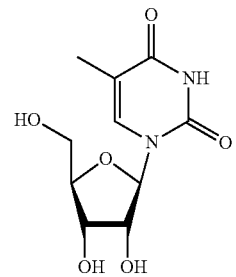

(a)

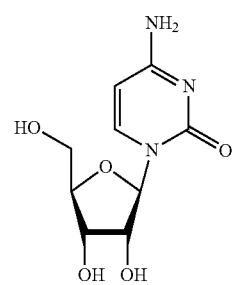

(b)

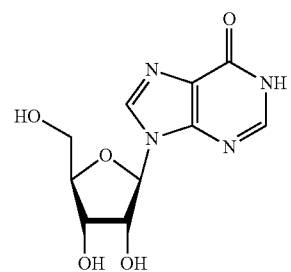

(c)

Molecular structures of (a) 5-methyluridine ($m^5U$), (b) cytidine (C), and (c) inosine (I)

Materials

All chemicals were purchased from Sigma-Aldrich (St. Louis, Mo.) at ACS grade or better, and were used without additional purification. Solvents and chemicals for the HPLC experiments were purchased at HPLC grade from Sigma-Aldrich. All of the aqueous solutions were prepared using Milli-Q water produced from a Synergy water system (Millipore) with a minimum resistivity of 18 MΩ·cm. All of the samples including the polypeptide samples were filtered through 0.2 µm filters before use unless otherwise indicated. 8 mL sample vials (National Scientific) were used for crystallization. All glassware and stir bars were first cleaned in a KOH/2-propanol bath. After rinsed with distilled water, the glassware and stir bars were soaked in 1 M HCl for 24 h and then rinsed with distilled water. Finally they were cleaned using RBS35 (Pierce), a surface-active detergent. After rinsed with distilled water and then with deionized water completely, the glassware and stir bars were air dried at room temperature before use.

AFP and Control Preparation

DAFP-1 was expressed and purified. The purified DAFP-1 was characterized using SDS-PAGE, MALDI-TOF mass spectrometer, CD spectrometry, and DSC and the identity of DAFP-1 was confirmed. The concentration of stock DAFP-1 solution was determined using a Cary 100 Bio UV-Vis spectroscopy (Varian) and the extinction coefficient of $5.47 \times 10^3 M^{-1} cm^{-1}$ at 280 nm was used.

BSA was purchased from Sigma-Aldrich (Item number A7030) and type III AFPs from fish were purchased from A/F Protein (Waltham, Mass.), which were used as received. The stock BSA and fish AFP solutions were prepared by weighing the solute and dissolving the solute in a known volume of water. The molecular weights, 66.5 kDa and 6.5 kDa, were used for BSA and type III fish AFPs, respectively. All of the weight measurements were carried out with an Ohaus Voyager Pro analytical and precision balance (Parsippany, N.J.).

Denatured DAFP-1 with completely reduced disulfide bonds was used as a second unknown and prepared following previously reported methods. To fully reduce all the disulfide bonds in DAFP-1, purified DAFP-1 (~1 mM) was incubated in 0.10 M sodium citrate, pH 3.0, and 15.0 mM tris(2-carboxyethyl)phosphine hydrochloride (TCEP) at 60° C. for 30 min. Then the denatured DAFP-1 was further purified using ÄKTA Purifier 10 (GE Healthcare) with a Sephacryl S-100 gel filtration column (GE Healthcare). In the denatured DAFP-1, all disulfide bonds were broken, resulting in the disruption of the structure of the conserved repeated threonine residues in the adjacent loops of DAFP-1 and thus the loss of the hydrogen bonding interactions with the m5U crystal surface.

Crystal Growth Procedure

We obtained the crystals of $m^5U$, C, and I, respectively, by evaporation of their aqueous solutions at room temperature. $m^5U$ was known to be crystallized from aqueous ethanol solutions. We found that $m^5U$ can crystallize from its aqueous solution directly. On day 1, each sample vial was first added 600 μL of 400 mM $m^5U$ solution. Then 20 μL of water or polypeptide solutions at certain concentrations were added into each vial. The final $m^5U$ concentration was 387 mM in each vial. The additive/$m^5U$ molar ratios ($\times 10^{-5}$) were varied from 0, 0.04, 0.4, 1.0, 1.2, 3.0, 4.0, 7.8, and 9.0. The vials were gently swirled after the addition and were left open in the air at the room temperature. At least three observations were recorded per day (every 8 hours) until the solutions in all the vials were dry. The experiments were repeated five times (Table 1).

TABLE 1

Sample results for crystal growth of $m^5U$ in the presence of AFPs in the absence of $m^5U$ seed crystals.

| Sample[a] | Polypeptide concentration (μM) | Induction time (day)[b] | Crystal quality[c] |
|---|---|---|---|
| $m^5U$ | 0 | 6 | Yes |
| $m^5U$ + BSA/denatured DAFP-1 | 70.0 | 6 | Yes |
| $m^5U$ + DAFP-1 | 70.0 | 13 | No |
| $m^5U$ + DAFP-1 | 35.0 | 11 | No |
| $m^5U$ + DAFP-1 | 30.0 | 10 | No |
| $m^5U$ + DAFP-1 | 15.0 | 10 | No |
| $m^5U$ + Type III AFP | 1.50 | 12 | No |
| $m^5U$ + Type III AFP | 0.15 | 12 | No |
| C | 0 | 13 | Yes |
| C + BSA/denatured DAFP-1 | 70.0 | 13 | Yes |
| C + DAFP-1 | 20.0 | 21 | No |
| C + DAFP-1 | 10.0 | 21 | No |
| C + Type III AFP | 20.0 | 20 | No |
| C + Type III AFP | 10.0 | 20 | No |
| I | 0 | 5 | Yes |
| I + BSA/denatured DAFP-1 | 70.0 | 5 | Yes |
| I + DAFP-1 | 2.0 | 15 | No |
| I + DAFP-1 | 0.5 | 15 | No |
| I + Type III AFP | 20.0 | 14 | No |
| I + Type III AFP | 10.0 | 13 | No |

[a]Each sample contained 387 mM $m^5U$, 252 mM C or 92 mM I on day 1. Results of each nucleoside alone and in the presence of each of the two polypeptide controls, BSA and denatured DAFP-1, were listed for comparison.
[b]The day that the first appearance of solid was observed.
[c]The suitableness of the resulting solids for single crystal x-ray diffraction. The identity and quality of single crystals of $m^5U$, C, and I were examined using polarized microscope, PXRD, and single crystal x-ray diffraction.

In previous reports, crystals of C were prepared by evaporating of its aqueous ethanol solutions. Here we obtained C crystals by evaporation of its aqueous solution. It is known that fast evaporation from the aqueous solutions of I usually resulted in a mixture of its aggregates, α-, β-, and γ-form crystals. By slowly evaporating its aqueous solution at 20° C., the pure α-form I crystals were obtained. The experimental procedures for C and I were similar to those described above for $m^5U$, while the concentrations of C and I solutions were 252 mM and 92 mM, respectively, in each sample vial on day 1 and the additive/C molar ratios ($\times 10^{-5}$) were varied from 0, 0.04, 0.4, 1.0, 1.2, 3.0, 4.0, 7.9, and 10.0 and the additive/I molar ratios ($\times 10^{-5}$) were varied from 0, 0.05, 0.5, 1.1, 2.2, 4.4, 8.1, 10.8, and 21.7. Photos of the vials were taken with a Canon EOS 30D camera during the crystallization process and when the process finished. Optical micrographs were taken under Nikon SMZ800 microscope with a Nikon Coolpix 5400 when the crystallization completed. The crystals were under Nikon SMZ800 microscope, and photos were taken by Nikon Coolpix 5400.

For the crystal habit study, crystallization conditions for the three nucleosides were used as described above. The formed nucleoside crystals in the absence of additives are homogeneous and reproducible with respect to their sizes and shapes. The same criterion was used for the study in the presence of each of the AFPs and controls. When the seed nucleoside crystals were first observed (less than 0.2 mg), DAFP-1 and type III AFP were added into the vials at final concentrations of 4.8 μM and 0.10 μM, respectively. Data were recorded as described above. The habit change can be stopped during the process. To stop the habit alteration, the mother liquor was removed from the vials and the seed crystals were washed quickly with cold water at 4° C. twice. The same volume of fresh saturated $m^5U$ solution as the removed mother liquor was added into the vial.

To make saturated thymine solution, an excess amount of thymine was first added into water and the resulting sample was shaken for two days and filtered. Then 20 μL of water or polypeptide solutions at certain concentrations were added into each vial with 1000 μL saturated thymine solution. The final thymine concentration was 2.94 mM in each vial and the final additive concentrations at the additive/thymine molar ratio of $1\times10^{-4}$ or above. All the above mentioned experiments were repeated five times.

HPLC Analysis

The resulting solids, both crystals and precipitates, were analyzed by HPLC. The HPLC analysis were performed on a Waters HPLC system consisting of a Waters 1525 binary HPLC pump, a BioSuite 125, 4 μm UHR SEC HPLC column (4.6×300 mm), and a Waters 2998 photodiode array detector. The SEC buffer contained 0.10 M $Na_2SO_4$, 0.10 M NaPi (pH 7.00), and 0.02% $NaN_3$. The solid $m^5U$ samples, each at a weight of 0.5±0.05 mg, were selected in at least four different locations in the same vial. The samples of precipitates were taken from the inside of solids. Each selected sample was dissolved in 100 μL HPLC buffer and diluted six-fold before HPLC analysis. For the solid thymine samples, the crystals were selected at three or more different locations in a vial. The selected crystals were dissolved in 1000 μL HPLC water and diluted to a final thymine concentration at about 0.600 mM. All the buffers and samples were filtered through a 0.1 μm filter and vacuum degassed before use. The flow rate was 0.30 mL/min at ambient temperature. The injection volume was 5.00 μL for all the HPLC experiments. Each experiment was repeated twice. Pure DAFP-1 and $m^5U$ were eluted at 11.5 and β 1 minutes, respectively. The HPLC analysis of all the thymine samples shows that only pure thymine was eluted at 14.5 minute.

X-ray Diffraction

All the resulting solids were sent to X-ray crystallography laboratory at the Beckman Institute of California Institute of Technology for analysis. The qualities of the solids for single crystal X-ray diffraction were determined (Table 1). The crystallographic data of $m^5U$ were from the $m^5U$ crystals grown in the presence of BSA. The resolution of the data was improved compared with that of previously reported data of $m^5U$. The crystallographic data of $m^5U$ have been deposited in the Cambridge Database (CCDC) and the CCDC deposit number is 835399.

Powder X-ray diffraction (PXRD) data were collected at room temperature on a Rigaku Mini Flex II desktop diffractometer using Cu Kα radiation (30 kV, 15 mA) with a 2θ range of 5°-50°, a step size of 0.010°, and a step time of 2 s. Samples were lightly ground by hand using a mortar and pestle. The same amount of the resulting powders were then mounted and analyzed on a front loading sample holder.

The identity and quality of the final obtained nucleoside solids for single crystal X-ray diffraction and PXRD were determined (Table 1). The PXRD patterns of the crystalline thymine obtained in the presence of the AFPs are in agreement with the reported pattern of crystalline thymine.

The resulting crystals of the three nucleosides appear as orthorhombic needles (FIGS. 1(a)-4(a)). The effect of a beetle AFP from *D. canadensis* (DAFP-1) on $m^5U$ crystal growth was first investigated. DAFP-1 is a β-helical repeat protein with a size of 9 kDa containing 8 disulfide bonds, which are important for its structure and function as antifreeze. DAFP-1 was studied previously for its antifreeze enhancement effect by small molecular enhancers and interactions between DAFP-1 and reduced nicotinamide adenine dinucleotide in solution have been demonstrated recently. To completely inhibit single crystal growth, a reasonable additive/nucleoside molar ratio (the critical ratio) is needed. The critical ratio is the minimum molar ratio required to completely inhibit the growth of crystals for a specific compound. Preferably, this ratio is chosen such that the compound precipitates in a crystalline form under the operating conditions used while minimizing the amount of crystal growth inhibitor present that is still capable of modifying the crystal habit of the precipitated compound to display the desired physical and chemical characteristics.

Different amounts of DAFP-1 were added directly to $m^5U$ solution to determine the critical ratio of DAFP-1/$m^5U$. The direct addition of DAFP-1 at all the tested concentrations delayed the first appearances of $m^5U$ precipitates in the solutions (Table 1), while higher additive/$m^5U$ molar ratios resulted in more significant delay. The critical ratio of DAFP-1/$m^5U$ was estimated to be $3.0\times10^{-5}$, where the ratio is at $3.0\times10^{-5}$ or higher, no single $m^5U$ crystal was detected, but reed-like amorphous $m^5U$ precipitates (Table 1 and FIG. 1(b)).

To further investigate how AFPs affect $m^5U$ crystal growth, DAFP-1 was added to the saturated $m^5U$ solutions in the presence of orthorhombic $m^5U$ seed crystals at the additive/$m^5U$ molar ratio of $1.2\times10^{-5}$. The growth of $m^5U$ crystals was able to continue, but with an apparent change in the crystal habit, from needle-shaped to normal orthorhombic (FIG. 1(c)).

Examining by x-ray crystallography, the crystalline $m^5U$ samples in FIG. 1(a) and FIG. 1(c) (have the same orthorhombic crystal structure, while no samples in FIG. 1(b) are suitable for single crystal x-ray diffraction. In the absence of DAFP-1, the propagation of the needle-like $m^5U$ crystals is along the a-axis. The crystal habit is determined by the relative growth rates of different crystal faces, suggesting that the altered crystal habit in the presence of DAFP-1 was caused by selective interaction of DAFP-1 with the (100) faces of $m^5U$ crystals (FIG. 5). The distance between the repeated oxygen atoms in the ribose moieties on the (100) face of the $m^5U$ crystal, 4.80 Å (FIG. 5(a)), matches well to 4.74 Å, the average distance of the hydroxyl oxygen atoms in conserved repeated threonine residues in adjacent loops of DAFP-1, suggesting hydrogen bonding interactions between the hydroxyl groups of the ribose moieties in the $m^5U$ crystal and conserved threonines in DAFP-1 (FIG. 12(a)). Due to such interactions, $m^5U$ crystal growth rate along the a-axis decreased to be less than those along the b- or c-axis, resulting in normal orthorhombic $m^5U$ crystals (FIG. 5(b)).

The powder X-ray diffraction (PXRD) patterns (FIG. 6(a) and FIG. 6(c)) of the single crystalline $m^5U$ samples in FIG. 1(a) and FIG. 1(c) show the same characteristic peaks assigned to the same unit cell. In contrast, few peaks of very low intensity were observed in the PXRD pattern (FIG. 6(b)) of the reed-like amorphous $m^5U$ precipitates in FIG. 1(b), suggesting that these solids lack well-ordered structures, and the few weak peaks that cannot be assigned to any known crystalline phase of $m^5U$ might result from a local order in these $m^5U$ samples. The PXRD results are in good agreement with the single crystal X-ray diffraction data. The finally obtained solids were also analyzed using high performance liquid chromatography (HPLC) to identify whether DAFP-1 presents in the samples. The HPLC analysis (FIGS. 7(b) and 7(c))) indicated the presence of both $m^5U$ and DAFP-1 in the samples in FIG. 1(b) and FIG. 1(c), suggesting that DAFP-1 is occluded in the reed-like amorphous $m^5U$ precipitates and the normal orthorhombic $m^5U$ crystals, which supports interactions between DAFP-1 and $m^5U$.

Under the same conditions, $m^5U$ crystal growth was also investigated in the presence of two controls, bovine serum albumin (BSA) and denatured DAFP-1 with complete reduction of its disulfide bonds, respectively. Neither BSA nor the denatured DAFP-1 inhibited or delayed the appearance of $m^5U$ precipitates at the control/$m^5U$ molar ratio of $1.8\times10^4$, a much higher ratio than those used for DAFP-1 (Table 1 and FIGS. 2(a)-(b))). The crystals were characterized to be $m^5U$ by X-ray crystallography and the results were confirmed by PXRD. HPLC analysis of these crystals revealed that only pure m⁵U presents, suggesting that the controls are simply excluded from the m⁵U crystals as impurities. These results indicate that the controls have no effect on the crystal growth of m⁵U.

To test the generality of the findings, the effect of DAFP-1 and the controls on the crystal growth of two other nucleosides, C and I, were examined. The space groups of m⁵U, C and I are all orthorhombic and repeated oxygen atoms in the hydroxyl groups in their ribose moieties are identified on their growing crystal faces, but the dimensions of the unit cells of these nucleosides are quite different. The two controls, BSA and the denatured DAFP-1, had no effects on the crystal growth of C and I. Interestingly, the effects of growth inhibition and habit modification were also observed for DAFP-1 on the crystal growth of C and I (FIGS. 3(d)-(g), FIGS. 4(d)-(g), FIGS. 8(b)-(c), and FIGS. 9(b)-(c)), suggesting that DAFP-1 can also interact with C and I crystals and such recognition can be flexible. The critical ratios of DAFP-1/C and /I were estimated to be $3.0 \times 10^{-5}$ and $0.5 \times 10^{-5}$.

To determine whether a different type of AFP can have similar effects, all the above experiments were carried out with a globular fish AFP, type III AFP. Similarly, direct additions of type III AFPs in the m⁵U, C, and I solutions effectively inhibited the crystal nucleation of m⁵U, C, and I, respectively (Table 1, FIGS. 2(c), 3(f), 4(f)). Additions of type III AFPs in the presence of the seed crystals of m⁵U, C, and I, altered the crystal habits of these nucleosides, respectively, and the resulting habits (FIGS. 2(d), 3(g) and 4(g) are similar to those caused by DAFP-1. However, we did not observe such inhibitory or crystal habit change effect of the AFPs on the crystal growth of thymine, the component base of m⁵U, under similar conditions (FIG. 10), suggesting that the hydroxyl containing ribose plays an important role in the recognition of m⁵U by AFPs.

Similarly, we crystallized trehalose dihydrate crystals by diffusing ethanol into the aqueous ethanol solution of trehalose directly. The protein:trehalose molar ratio ($\times 10^{-5}$) was 9.0 in FIG. 24(b) The crystals formed in the presence of DAFP-1 show a dramatic decrease in size as compared to the crystals obtained without additive.

To further test the effect of AFP on different types of compounds, we tested copper sulfate pentahydrate. The crystal grows from copper sulfate pentahydrate aqueous solutions at room temperature. Seventy milligrams of copper sulfate pentahydrate were dissolved in one milliliter of deionized, milli-Q water. The solution was filtered and left in the air for evaporation. In the presence AFPs, the conditions were all the same except DAFP-1 was added to the solution at the molar ratio of $10^{-7}$ to copper sulfate. The presence of the AFP significantly delayed the appearance of the crystal for several days (from 7 days to 11 days) and the resulting crystals were found with dramatically decreased sizes (FIG. 25).

EXAMPLE 2

AFP can be used to control the crystallization of 5-methyluridine (m⁵U) and produce a new thermodynamically and kinetically less preferred crystal form, which is significantly less likely to be suitable for undesirable chemical and/or physical processes. We show selective nucleation and growth of a previously unknown, dihydrate crystalline form of 5-methylurudine (m⁵U) using a novel efficient protein additive, antifreeze protein (AFP). AFP can selectively inhibit the appearance of the hemihydrate form of m⁵U (form I), the only previously known crystalline form of m⁵U, and hence allows the growth of m⁵U dihydrate crystal (form II), the pure form of which cannot grow directly from m⁵U supersaturated solutions under the same conditions. The two forms obtained herein were characterized using X-ray crystallography and differential scanning calorimetry (DSC). Compared to the hemihydrate form, the block-like dihydrate crystalline form of m⁵U is thermodynamically and kinetically less preferred. A mechanism, supported by both experimental and theoretical results, was proposed for the AFP-induced selection process. The results suggest that crystallization processes using AFPs may be valuable for selective growth of hydrates and polymorphs of hydroxyl compounds. Furthermore, insights into the antifreeze mechanism of AFPs were provided.

The only previously known crystalline form of m⁵U is its hemihydrate crystal, designated form I, which was crystallized exclusively by evaporation from the supersaturated aqueous solutions. By using DAFP-1 as an additive, remarkably, we were able to control the crystallization of m⁵U and discover a new, less thermodynamically and kinetically preferred form, m⁵U dihydrate crystal, designated form II. Forms I and II crystals are readily distinguished from each other by their morphology and stability. Form I crystals are needle-like in appearance (FIG. 16(a)) and there was no change (in the appearance, single crystal X-ray diffraction pattern, or DSC profile) of the crystals after being left in air at room temperature for more than 24 months. Form II crystals are block-shaped (FIG. 16(b)) and became white opaque powders/blocks in 2 months. The resulting solids were not suitable for single-crystal X-ray diffraction.

Both thermodynamic analysis and kinetics analysis show the possibility of the AFP induced selective crystallization of the less thermodynamically and kinetically preferred m⁵U dihydrate crystal and gives insights into this process.

Thermodynamic Analysis.

According to the Gibbs-Volmer theory of homogeneous nucleation, the overall free energy change, $\Delta G$, between a small nucleus of m⁵U and m⁵U in aqueous solution is equal to the sum of the surface excess free energy, $\Delta G_s$, and the volume excess free energy, $\Delta G_v$. Therefore, $$\Delta G_i(r_i) = \Delta G_{si} + \Delta G_{vi} \qquad (1)$$

where i=I or II, representing form I or form II of m⁵U. $\Delta G_{si}$ is a positive quantity, while $\Delta G_{vi}$ is a negative quantity. For simplicity, a nucleus of m⁵U is assumed to be a sphere with a radius, r.

Then, $$\Delta G_i(r_i) = 4\pi r_i^2 \gamma_i + (4\pi r_i^3 \Delta G_{vi})/3 \qquad (2)$$

where, $\gamma_i$ is the interfacial tension between the developing crystalline surface and the supersaturated solution where the nucleus is located. The critical nucleus, $r_{ci} = -2\gamma/\Delta G_{vi}$, is obtained at $d\Delta G_i(r_i)/dr_i = 0$.

At the critical m⁵U form I nucleus, we get $$\Delta G_{cI} = (4\pi \gamma_I r_{cI}^2)/3. \qquad (3)$$

DAFP-1 can bind to m⁵U form I nucleus. For the AFP attached form I nuclei, $$\Delta G_{cI'} = F(4\pi \gamma_I r_{cI}^2)/3 \qquad (4)$$

where I' is m⁵U form I nucleus with AFP attachment and F is a correct factor resulting from the AFP attachment of m⁵U form I nucleus. To inhibit m⁵U form I nucleation and crystal growth, we need F>1 and hence $\Delta G_{cI'} > \Delta G_{cI}$.

At the critical m⁵U form II nucleus, we get $$\Delta G_{cII} = (4\pi \gamma_{II} r_{cII}^2)/3 \qquad (5)$$

To make the less preferred m⁵U form II nucleation and crystal growth occur before m⁵U form I nucleation and crystal growth, we need $\Delta G_{cI} > \Delta G_{cII}$, that is $F > (\gamma_{II} r_{cII}^2)/(\gamma_I r_{cI}^2)$.

The hydrophilic face of the AFP can bind to the thermodynamically preferred, form I nuclei of m⁵U. The hydrophobic face of the AFP thus exposes to bulk solution, which results in large repulsive interactions against incoming m⁵U molecules and hence inhibits form I crystallization. In other words, enthalpic contribution leads F>1. However, DAFP-1 cannot bind to m⁵U form II nuclei. The total contributions from F, interfacial tension and the radius of nuclei, finally lead to the nucleation of the metastable crystalline. At this point, the free energy of form I nuclei with AFP attachment is still higher than that of crystalline form II. This finally allows the thermodynamically less preferred dihydrate crystalline form to fully grow.

Kinetic Analysis.

$J_i$ is the nucleation rate of form I crystal. The kinetic coefficient for form i crystal growth is $k_i$. For a system with two forms of potential crystals, i.e., m⁵U crystalline forms I and II, the following condition must be held to have m⁵U crystalline form II as the only crystallization product, $$J_{II} k_{II}^3 >> J_I k_I^3 \quad (6)$$

This suggests that the appearance of different structures may be influenced by additives designed to interfere selectively with either the nucleation, growth rates of a particular phase or both.

According to Arrhenius equation, the rate of nucleation can be expressed as $$J_i = A_i \exp(-\Delta G_{ci}/kT) = A_i \exp[-(16\pi\gamma_i^3 v_i^2)/(3k^3 T^3 \{\ln S_i\}^2)] \quad (7)$$

where $A_i$ is Arrhenius pre-exponential factor for species i, k is the Boltzmann constant. T is the temperature in kelvins, $v_i$ is the molecular volume for species i, $S_i$ is supersaturation of the species i.

In the absence of AFPs, only m⁵U form I crystals can form. Thus, $$J_I k_I^3 >> J_{II} k_{II}^3 \quad (8)$$

In the presence of AFPs, AFPs inhibit the form I nucleation. Therefore, $J_{I'} \rightarrow \rightarrow 0$ and $JJ_{II} >> J_{I'}$, and we get $$J_{II} k_{II}^3 >> J_{I'} k_{I'}^3 \rightarrow \rightarrow 0 \quad (9)$$

Under this kinetic condition described in the above equation, we can exclusively obtain the kinetically less preferred m⁵U crystalline form II.

Structure Aspects.

The structures of both forms were determined by single-crystal X-ray diffraction (FIGS. 17(a)-(b)). Both forms crystallize in the orthorhombic crystal system. Form I was solved in the space group P2₁2₁2, whereas the new form is in P2₁2₁2₁ (Table 2). A high degree of torsional freedom of the N1-C6 bond is in the m⁵U molecule.

TABLE 2

Crystallographic Data for the Hemihydrate (Form I) and Dihydrate (Form II) of 5-Methyluridine

| parameter | form I | form II |
| --- | --- | --- |
| formula | C10H14N2O6 · 0.5H2O | C10H14N2O6 · 2H2O |
| formula weight | 267.24 | 294.26 |
| temperature (K) | 90(2) | 100(2) |
| crystal system | orthorhombic | orthorhombic |
| space group | P21212 | P212121 |
| a/Å | 13.953(2) | 6.75400(10) |
| b/Å | 17.201(3) | 8.83730(10) |
| c/Å | 4.8017(7) | 20.9847(3) |
| α = β = γ | 90° | 90° |
| cell volume/Å³ | 1152.4(3) | 1252.52(3) |
| calc density/g cm⁻³ | 1.540 | 1.560 |
| Z | 4 | 4 |
| data/restraints/parameters | 1941/5/184 | 2199/10/206 |
| final R indices for I > 2σ(I) | R1 = 0.0274 | R1 = 0.0282 |
|  | wR2 = 0.0730 | wR2 = 0.0741 |

Figure 18:
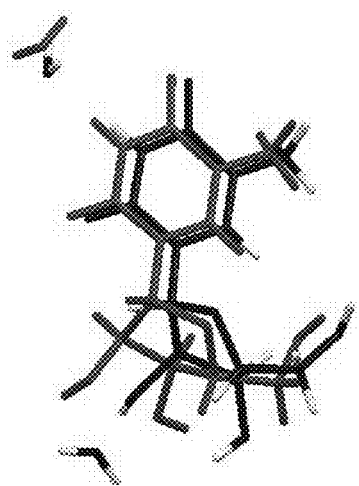
FIG. 18 shows overlay of unique molecules in the crystal structure of $m^5U$ form I (all in gray) and form II (all in gray, except hydrogen atoms in light gray). Representative molecules in (a) $m^5U$ form I ($m^5U$ hemihydrate; all are in a red color) and (b) $m^5U$ form II ($m^5U$ dihydrate; all are in a blue color except that hydrogen atoms are in a gray color).

The overlap of m⁵U molecules in form I and form II reveals a significant conformational difference in the ribose moiety (FIG. 18). Such change may allow optimization of hydrogen bonds between the hydroxyl groups in the ribose moiety and neighboring groups in m⁵U and water.

Water molecules are hydrogen bound to m⁵U molecules through N—H . . . O and O—H . . . O interactions. Comparing to those in form I, the number of strong intermolecular hydrogen bonds between two m⁵U molecules decreases, whereas the number of hydrogen bonds between m⁵U and water molecules increases in form II (Table 3). The strong intermolecular hydrogen bonds between two m⁵U molecules in form I are disrupted upon the introduction of additional water molecules. Consequently, the packing motifs of the two forms of m⁵U are different (FIGS. 19(a)-(d)).

TABLE 3

Geometrical Parameters for Hydrogen Bonding Interactions in Forms I and II of 5-Methyluridine

| form | D-H...A[a] | d(D-H) (Å) | d(H...A) (Å) | d(D...A) (Å) | <(DHA) (°) |
| --- | --- | --- | --- | --- | --- |
| form I[b] | O(4)-H(4O)...O(5)[i] | 0.886(15) | 1.881(15) | 2.7658(15) | 175.3(17) |
|  | O(5)-H(5O)...O(2)[ii] | 0.840(15) | 1.887(15) | 2.7158(15) | 168.7(18) |
|  | O(6)-H(6O)...O(1)[iii] | 0.833(15) | 1.890(15) | 2.7097(14) | 167.6(19) |
|  | O(7)-H(7O)...O(6) | 0.860(14) | 2.023(14) | 2.8722(13) | 169.2(18) |
|  | N(2)-H(2N)...O(7)[iv] | 0.889(14) | 2.106(15) | 2.9764(13) | 166.0(17) |
| form II[c] | O(4)-H(4O)...O(8) | 0.838(16) | 1.853(16) | 2.6902(15) | 177(2) |
|  | O(5)-H(5)...O(7)[i] | 0.86(2) | 2.09(2) | 2.8868(15) | 154.2(19) |
|  | O(6)-H(6O)...O(2)[ii] | 0.865(16) | 1.957(17) | 2.7954(16) | 163(2) |
|  | O(7)-H(7WB)...O(5)[iii] | 0.846(15) | 2.073(15) | 2.9103(17) | 170.0(19) |

TABLE 3-continued

Geometrical Parameters for Hydrogen Bonding
Interactions in Forms I and II of 5-Methyluridine

| form | D-H...A[a] | d(D-H) (Å) | d(H...A) (Å) | d(D...A) (Å) | <(DHA) (°) |
|---|---|---|---|---|---|
| | O(8)-H(8WA)...O(5)[iv] | 0.848(15) | 2.041(16) | 2.8510(16) | 159(2) |
| | O(8)-H(8WB)...O(1)[v] | 0.862(15) | 1.926(15) | 2.7783(16) | 169.9(19) |
| | N(2)-H(2N)...O(7) | 0.854(14) | 2.049(15) | 2.9016(16) | 177.2(19) |

[a]D = Donor, A = Acceptor.
[b]Symmetry transformations used to generate equivalent atoms:
[i]-x + 1, -y + 1, z;
[ii]-x + ½, y - ½, -z + 1;
[iii]x - ½, -y + 3/2, -z;
[iv]-x + ½, y + ½, -z.
[c]Symmetry transformations used to generate equivalent atoms:
[i]-x + 3/2, -y + 1, z - ½;
[ii]-x, y + ½, -z + ½;
[iii]-x + 1, y + ½, -z + ½;
[iv]x + ½, -y + ½, -z;
[v]-x + 2, y - ½, -z + ½.

Figure 19:
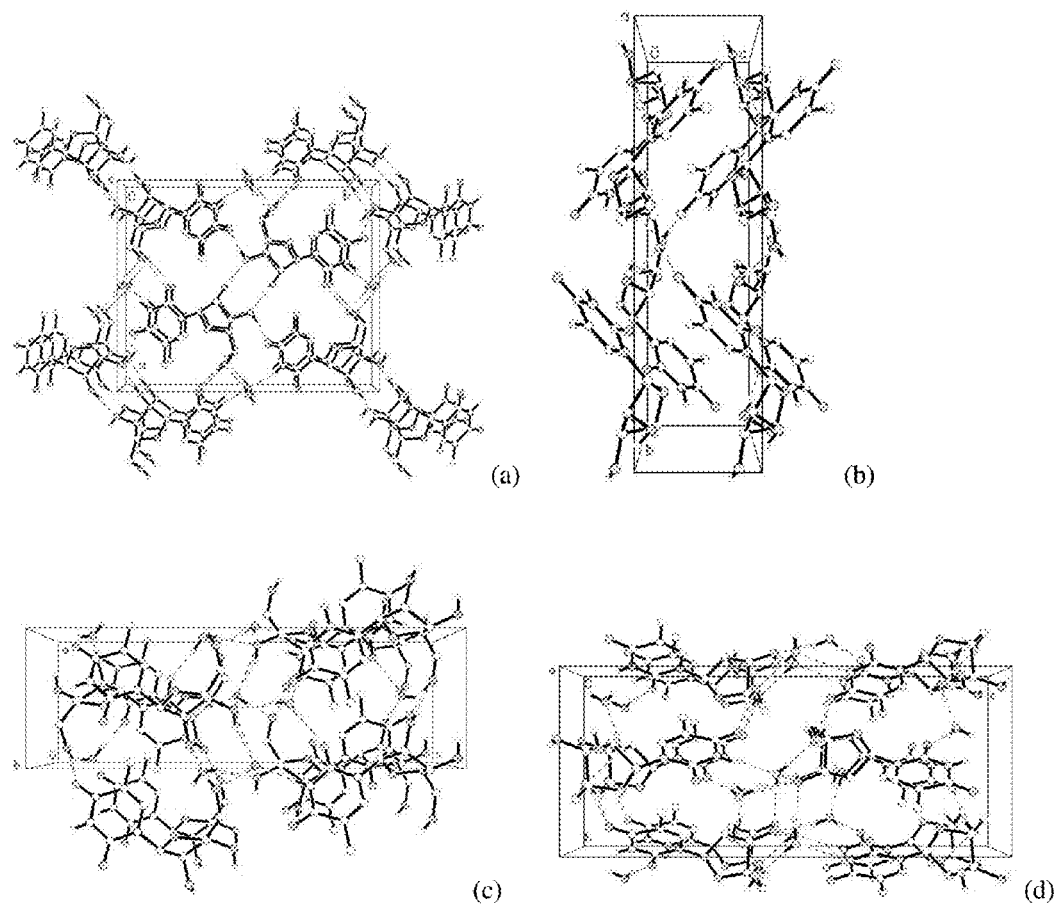
FIGS. 19(a)-(d) show packing diagrams of $m^5U$ form I (a and b) and form II (c and d). Dotted lines represent intermolecular hydrogen bonding in the crystals.

All the growing faces in form I crystal contain potential hydrogen bond donor or acceptor atoms (FIGS. 19(a)-(b)). On the (100) face, there are three oxygen atoms from the thymine moiety (O1), a hydroxyl group in the ribose moiety (O4), and water (O7), respectively, with the smallest possible repeating distance of 4.80 Å (or 17.20 Å) along c (or b) dimension (Table 2 and FIG. 19(a)-(b)). Two oxygen atoms from a hydroxyl group in the ribose moiety (O5) and water (O7), respectively, are on the face (O10) with the smallest possible repeating distance being 4.80 Å (or 13.96 Å) along c (or a) dimension (Table 2 and FIG. 19(a)-(b)). The oxygen atom in the thymine moiety (O1) is on the face of (001) repeating with the smallest possible distances of 13.95 Å (or 17.20 Å) along a (or b) dimension (Table 2 and FIG. 19(a)-(b)). In contrast to form I, the three growing faces of form II are more hydrophobic. No potential hydrogen bond donor or acceptor atom is observed on the face of (010) or (001); and the oxygen atoms (O7 and O8) of the two water molecule are on the (100) face both with the smallest repeating distance of 8.83 Å (or 20.98 Å) along b (or c) dimension, but the possible repeating distances are not even close to 4.80 Å (Table 2 and FIG. 19(c)-(d)).

Hydrogen bonding interactions are known to be essential in some AFPs to recognize ice crystals and the distance of the side chain hydroxyl groups in the conserved repeat residues in the AFPs matches that of repeating oxygen atoms on the prism face of the normal ice crystal. DAFP-1 is a repeat protein with conserved threonines as putative ice-binding residues in each repeat unit, and according to the modeled structure of DAFP-1, the average distance of the side-chain oxygen atoms in the threonines in the adjacent loops is 4.74 Å (FIG. 12 (a). It is remarkable that the distance matches well to the unit-cell dimension along the c axis in form I, 4.80 Å, with reasonable flexibility.

Oxygen atoms with a possible repeating distance of 4.80 Å are on the fast-growth (100) face and the (010) face in form I, suggesting that DAFP-1 can recognize these faces through hydrogen bonding interactions. However, DAFP-1 cannot interact with any face of m⁵U form II crystal due to the lack of match of possible hydrogen bond donor/acceptor atoms in DAFP-1 and the growing faces of form II. Therefore, DAFP-1 can selectively inhibit form I crystallization, but allow the growth of form II crystal.

The interactions between DAFP-1 and $m^5U$ are highly efficient since only a tiny amount of DAFP-1 as additives is needed (the additive/$m^5U$ molar ratio was $5×10^{-6}$). Moreover, such interactions need to be weak in order to guide the crystal growth. The selective crystallization of form II by using DAFP-1 cannot be obtained if the interactions between DAFP-1 and $m^5U$ are strong. This is because if the interactions between DAFP-1 and $m^5U$ are strong, some $m^5U$ molecules must bind to DAFP-1 completely in solution, leaving the rest pure $m^5U$ and finally resulting in form I only.

Figure 20:
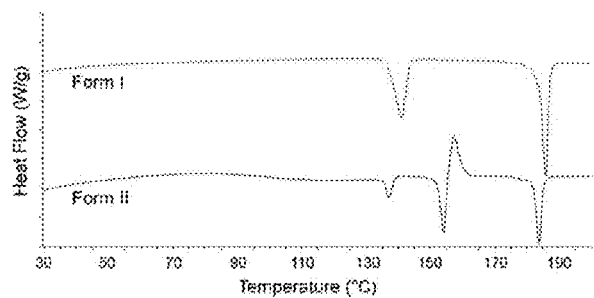
FIG. 20 shows DSC thermograms (exo up) of form I (a) and form II (b) of $m^5U$.

Thermodynamic Stability Analysis. Both forms of $m^5U$ were analyzed by DSC (FIG. 20). Form I displays two endothermic events upon heating. The first endotherm associated with water loss is at 139.07° C., whereas the second endotherm ascribed to the melting is at 185.65° C. Form II exhibited two endotherms at 137.04° C. and 153.72° C., respectively, for the loss of the two water molecules, followed by a recrystallization exotherm at 157.66° C. and then a melting endotherm at 183.41° C. Form II starts losing water and then melts at relatively lower temperatures than those of form I. The enthalpy profiles for both forms are compared in FIG. 21. Form I is more thermodynamically stable, which is in accordance with the previous observations.

Figure 21:
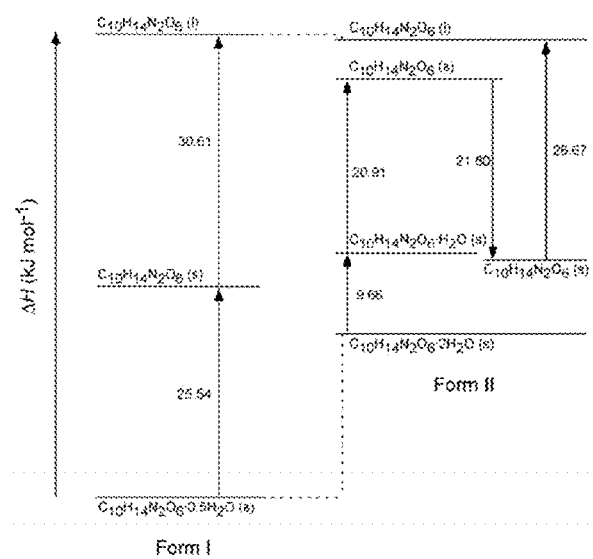
FIG. 21 shows comparison of relative enthalpies for the phase transitions of form I and form II $m^5U$.

The crystallization processes of both forms were carried out at ambient conditions. We assume that the reaction of form II becoming form I by losing water at room conditions, i.e., $m^5U$ form II→$m^5U$ form I+1.5 $H_2O$. Heat is needed to cause the dihydate form II to lose water and become the hemihydrate form I (FIG. 21). Therefore, the ΔH for the reaction is positive, i.e., $$\Delta H > 0 \qquad (10)$$

At room temperature, T, we have $$d(\Delta G/T)dT = -\Delta H/T^2. \qquad (11)$$

For a tiny temperature increase, dT, the resulting temperature, T' can be expressed as T'=T+dT and $$T' > T. \qquad (12)$$

Assuming that ΔG is a constant for such a tiny change, we obtain $$\Delta G(d1/T) = -\Delta H/T^2 dT. \qquad (13)$$

By integrating the above equation, we get $$\Delta G(\ln T'/T) = \Delta H(1/T' - 1/T). \qquad (14)$$

Combining Eqs. 10, 12, 14, we obtain ΔG<0. Therefore, the free energy change of the form II to I transition at room containing is negative. That is form I crystal is more thermodynamically stable. The results are consistent with the observations that form I crystals were stable in air for at least 2 years, while form II crystals became white powders/blocks in 2 months in air.

Crystallization Kinetics Analysis.

In the absence of DAFP-1, form I starts growing on day 3 and the crystallization completes on day 9 (FIG. 22). DAFP-1 can inhibit the crystallization of form I. In the presence of DAFP-1, only form II can be grown and the crystallization starts on day 6 and finishes on day 15. The crystallization of form II cannot happen in the absence of DAFP-1, since the crystallization of form I has much faster kinetics than that of form II. However, the presence of DAFP-1 completely inhibits the fast growing form I and hence results in the exclusive formation of the new, slow growing form II. The average crystal growth rate of form II is estimated to be 10.5% per day, which is slower than that of form I, 13.3% per day.

Mechanism of AFP-Induced Selective Nucleation and Growth.

Our approach with regard to the mechanism of the AFP-induced control of crystallization rests on the assumption that supersaturated solutions contain nuclei adopting similar arrangements to the final crystal structure. This assumption has been successful in designing tailor-made inhibitors.

In the supersaturated solution of $m^5U$, form I nuclei whose structure are similar to that of form I crystal are evolved around day 2 (FIG. 22-FIG. 23($a$)). In the absence of DAFP-1, form I crystal grows. As suggested by the match between the hydroxyl groups in the conserved threonines in DAFP-1 and the hydrogen bond donor/acceptor atoms on the growing faces of (100) and (010) in form I of $m^5U$, DAFP-1 can recognize the fast growing face of (100) and the (010) face of form I through hydrogen bonding interactions. Hence, form I nuclei can be completely inhibited in the presence of DAFP-1 and then the extent of supersaturation increases during the following days until the crystallization of form II around day 5 (FIG. 22-FIG. 23($b$)). That is the higher degree of supersaturation attained in the presence of DAFP-1 is required for the formation of form II nuclei. In addition, due to the mismatch between the hydrogen bond donor/acceptor atoms in DAFP-1 and in the growing faces of form II, DAFP-1 cannot interact with the newly formed form II nuclei. Consequently, only form II grows, even though it is a thermodynamically and kinetically less preferred phase.

DAFP-1 can induce $m^5U$ to crystallize into a thermodynamically and kinetically less preferred dihydrate form and the structure analysis suggests that the mechanism of AFP-induced crystallization control of $m^5U$ is similar to that of antifreeze action of AFPs. One can view all ice polymorphs as "ice hydrates" since water molecule itself is the building unit of ice. Ice $I_h$ is the most common form of ice, which is highly stable and the most dangerous to life. The action of AFPs on ice can be similar to that on $m^5U$. AFPs may induce the crystallization of water into new ice polymorph(s), which are thermodynamically and kinetically less preferred ice polymorph(s) of ice comparing to the common, highly stable $I_h$. The AFP-induced new ice polymorph(s) readily melt, and hence the net effect is antifreeze.

Materials and Methods

Chemicals were purchased from Sigma-Aldrich (St. Louis, Mo.) at ACS grade or better and used as received Milli-Q water produced from a Synergy water system (Millipore) with a minimum resistivity of 18 MΩ·cm was used for making solutions. All the sample solutions were filtered through 0.2 μm filters before use. Sample vials (10 mL, National Scientific) were used for crystallization. Glassware and stir bars were cleaned as previously described.

Synthesis

Figure 15:
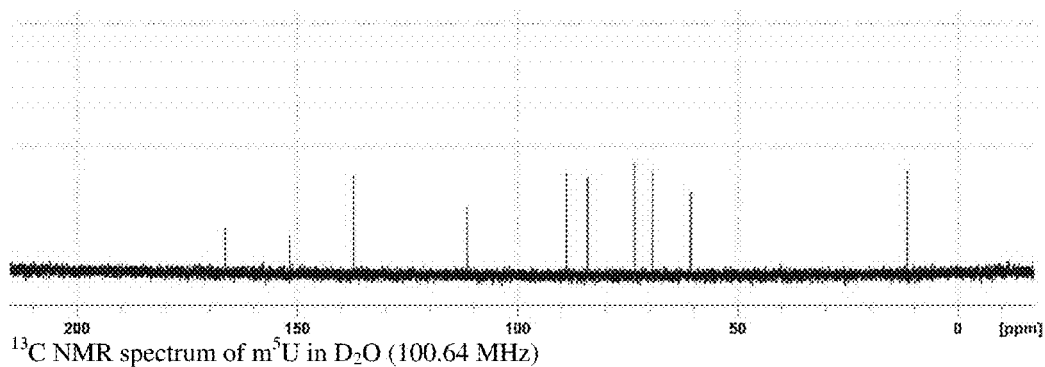
FIG. 15 shows $^{13}C$ NMR spectrum of the product ($m^5U$) in $D_2O$ (100.64 MHz)

The syntheses of o,o'-bis(trimethylsilyl)thymine and 5-methylurine used the following procedures modified from previous methods (FIG. 13). Trimethylchlorosilane (6.51 g, 0.06 mole) and thymine (3.78 g, 0.03 mole) were suspended in 100 mL dry benzene. The suspension was quickly stirred under $N_2$ and 8.25 mL triethylamine in benzene was added dropwise. The mixture was then refluxed for 2 hours. O,O'-Bis(trimethylsilyl)thymine was crystallized upon standing at room temperature. After recrystallization for three times, the pure o,o'-bis(trimethylsilyl)thymine (7.55 g, yield 93%) appeared as slightly yellow crystals. Then, the obtained o,o'-bis(trimethylsilyl)thymine (11.90 g, 0.044 mole, 10% excess) and β-D-ribofuranose 1-acetate 2,3,5-tribenzoate (20.18 g, 0.04 mole) were first mixed in 80 mL $CH_3CN$ under $N_2$. The mixture temperature was kept at 0° C. and stirred. $SnCl_4$ (41.34 mL of 1.0 M) in methylene chloride was added dropwise. The reaction was run at 0° C. for 2 hours and warmed up to room temperature for another hour. $KHCO_3$ (60 g) in 60 mL water was added to remove the trimethylsilyl protected group. The solvents were removed under reduced pressure at 60° C. The product was a white solid or crystals after silica gel chromatography using EtOAc in $CH_2Cl_2$ as eluent and the formation was revealed by TLC analysis ($R_f$=0.60) using 20% EtOAc in $CH_2Cl_2$. Sodium ethoxide in ethanol (668 mL, 21% w/v) was used to remove the Bz protecting group. The solvents were removed under reduced pressure at 50° C. The product was a white solid or crystals after silica gel chromatography using ethanol in $CH_2Cl_2$ as eluent and the formation was revealed by TLC analysis ($R_f$=0.70) using 25% EtOAc in $CH_2Cl_2$ and LC/ESI-MS and NMR (FIG. 14 and FIG. 15).

Preparation of Antifreeze Protein

DAFP-1 was expressed and purified as described previously. The purified protein was characterized using SDS-PAGE gel electrophoresis, MALDI-TOF mass spectrometer, circular dichroism (CD) spectrometry, and differential scanning calorimetry (DSC), respectively, as previously described and the identity of DAFP was confirmed. The concentration of stock DAFP-1 solution was determined using a Cary 100 Bio UV-Vis spectroscopy (Varian) and the extinction coefficient of $5.47 \times 10^3$ $M^{-1}$ $cm^{-1}$ at 280 nm was used.

Crystallization

Supersaturated $m^5U$ aqueous solutions (0.6 M) were made at 30° C. and filtered as soon as possible. Crystals were not grown after the temperature dropped to room temperature for a few days. On day 1, to each sample vial was added 600 μL of 0.6 M $m^5U$ solution, and then 5 μL of water or DAFP solution were added into the vial. The vials were gently swirled after the additions. The resulting $m^5U$ concentration was 595 mM in each vial and additive/$m^5U$ molar ratios ($\times 10^{-6}$) were either 0 or 5. The sample vials were left open in the air at room temperature and three observations at least were recorded per day (every 8 hours) until the solutions in all the vials were dry. The above experiments were repeated five times. Optical micrographs were taken under Nikon SMZ800 microscope with a Nikon Coolpix 5400 when the crystallization completed.

Crystallization Kinetics

Under the above conditions, only form I crystalline $m^5U$ was able to grow in the absence of DAFP-1; however, in the presence of DAFP-1, form II crystalline $m^5U$ was grown exclusively. The kinetics of crystallization of $m^5U$ form I and form II, respectively, was estimated based on the rate of the weight of the occurring crystals and the initial weight of $m^5U$ in the specific vial. All the liquid in the vial was collected gently and the weight of the vial or the vial with crystals was measured. After the measurement, the collected liquid was put back into the vial and the crystallization continued. The weights were measured on an Ohaus Discovery semi-micro analytical balance at 9 am every day until the crystallization finished. The experiments were repeated on three vials and the average values were reported.

Single Crystal X-Ray Diffraction

Colorless crystal of m$^5$U form I was mounted on a Cryoloop with Paratone-N oil and data was collected at 90K with a Bruker APEX I CCD using Cu K alpha radiation generated from a rotating anode. In a similar fashion, a colorless crystal of m$^5$U form II was mounted on a Cryoloop with Paratone-N oil and data was collected at 100 K with a Bruker APEX II CCD using Cu K alpha radiation generated from a rotating anode. For both crystals data were corrected for absorption with SADABS and structures were solved by direct methods. All non-hydrogen atoms were refined anisotropically by full matrix least squares on F2. Hydrogen atoms on 0 and N atoms were found from Fourier difference maps and were refined isotropically with distances of O—H and 0.85 (0.02) or 0.86 (0.02) Å and N—H distance 0.87 (0.02) Å and at 1.20 or 1.50 Ueq parent atom. All other hydrogen atoms were placed in calculated positions and refined as riding models with C—H distances of 0.950 Å (CHar), 1.000 Å, (CH), 0.990 Å (CH$_2$), 0.980 Å (CH$_3$) and at 1.20 or 1.50 Ueq of parent C atom. Flack parameters for m$^5$U forms I and II were −0.0187 and −0.1358. Bruker suite of X-ray data collection (APEX2 and SAINT), and Shelrick's processing and refinement programs (SHELXS97, SHELXL97, SHELXTL) were used for these structural determinations. The crystallographic data of m$^5$U forms I and II have been deposited in the Cambridge Database (CCDC) and the CCDC deposit numbers are 916820 and 916088, respectively.

Differential Scanning Calorimetry (DSC)

All experiments were performed with a DSC 1 (Mettler Toledo, Ohio). An indium standard (Mettler Toledo, Ohio) was used to calibrate the instrument. Samples weighed 3-4 mg and were hermetically encapsulated in standard aluminum sample pans with pierced lids to release any pressure build-up during the experiments. The samples were heated from 25 to 200° C. at a rate of 5° C./min.

The invention claimed is:

1. A method of using an antifreeze protein (AFP) to inhibit the nucleation and crystallization of a nucleoside compound from a solution comprising:
    obtaining a solution containing the nucleoside compound and an effective amount of at least one AFP, wherein the nucleoside compound can crystallize into an orthorhombic structure in the absence of AFP.

2. The method of claim 1, wherein the AFP is selected from the group consisting of natural or engineered antifreeze proteins, antifreeze polypeptides and antifreeze peptides, active fragments of antifreeze proteins, antifreeze polypeptides and antifreeze peptides, mimetics of antifreeze proteins, antifreeze polypeptides and antifreeze peptides, their active mimetic fragments, and combinations thereof.

3. The method of claim 1, wherein the nucleoside compound is selected from the group consisting of 5-methyluridine, cytidine, inosine, derivatives thereof, and combinations thereof.

4. The method of claim 1, wherein the AFP is either beetle *D. canadensis* AFP (DAFP-1) or globular fish AFP type III, wherein the nucleoside compound is selected from the group consisting of, 5-methyluridine, cytidine, inosine, derivatives thereof, and combinations thereof, wherein the ratio of the AFP to the nucleoside compound is about or less than about 0.05% by weight; and
    wherein said method ensures the inhibited nucleation and crystallization affects about 100% of the total amount of the nucleoside compound.

5. A method of using an antifreeze protein (AFP) to alter the crystalline shape of a nucleoside compound formed from a solution comprising:
    substantiating a first crystalline shape-of a nucleoside compound, wherein the nucleoside compound can crystallize into an orthorhombic structure in the absence of AFP, and wherein the nucleoside compound was crystallized into the first crystalline shape in the absence of AFP;
    obtaining a solution containing the nucleoside compound;
    confirming a seed crystal of the nucleoside compound is in the solution;
    adding an effective amount of at least one AFP to the solution, wherein the seed crystal is present and wherein the ratio of AFP to the nucleoside compound is about or less than about 0.05% by weight;
    verifying that the nucleoside compound forms solid crystals having a second crystalline shape that is different from the first crystalline shape; and
    ensuring that about 100% of the formed solid crystals have the second crystalline shape.

6. The method of claim 5, wherein the AFP is selected from the group consisting of natural or engineered antifreeze proteins, antifreeze polypeptides and antifreeze peptides, active fragments of antifreeze proteins, antifreeze polypeptides and antifreeze peptides, mimetics of antifreeze proteins, antifreeze polypeptides and antifreeze peptides, their active mimetic fragments, and combinations thereof.

7. The method of claim 5, wherein the nucleoside compound excludes ice and gas hydrates.

8. A 5-methyluridine dihydrate crystal having an orthorhombic unit cell, wherein the unit cell has a first dimension measuring about 6.75 Å, a second dimension measuring about 8.84 Å, and a third dimension measuring about 20.98 Å, wherein the angle between the second dimension and the third dimension is about 90 degrees, wherein the angle between the third dimension and the first dimension is about 90 degrees, and wherein the angle between the first dimension and the second dimension is about 90 degrees.

9. Compositions comprising a 5-methyluridine dihydrate crystal, as claimed in claim 8.

10. A method of using an antifreeze protein (AFP) to produce a 5-methyluridine dihydrate crystal comprising:
    obtaining a supersaturated 5-methyluridine aqueous solution with an effective amount of at least one AFP in the solution, wherein the ratio of AFP to 5-methyluridine is about or less than about 0.05%; and
    ensuring the 5-methyluridine dihydrate crystal is a blocky shape, wherein the length of the longest side of each of the 5-methyluridine dihydrate crystal is no shorter than about 1000 micrometers, and wherein the length of the shortest side of the 5-methyluridine dihydrate crystal is no shorter than about 500 micrometers.

11. The method of claim 10, wherein the AFP is selected from the group consisting of natural or engineered antifreeze proteins, antifreeze polypeptides and antifreeze peptides, active fragments of antifreeze proteins, antifreeze polypeptides and antifreeze peptides, mimetics of antifreeze proteins, antifreeze polypeptides and antifreeze peptides, their active mimetic fragments, and combinations thereof.

* * * * *